US011878066B2

(12) United States Patent
Perfect et al.

(10) Patent No.: US 11,878,066 B2
(45) Date of Patent: Jan. 23, 2024

(54) COMPOSITION AND METHOD FOR DETECTION OF DEMINERALISATION

(71) Applicant: Calcivis Limited, Edinburgh (GB)

(72) Inventors: Emma Perfect, Edinburgh (GB); Chris Longbottom, Newport-on-Tay (GB)

(73) Assignee: Calcivis Limited, Edinburgh (GB)

( * ) Notice: Subject to any disclaimer, the term of this patent is extended or adjusted under 35 U.S.C. 154(b) by 0 days.

(21) Appl. No.: 15/857,470

(22) Filed: Dec. 28, 2017

(65) Prior Publication Data

US 2018/0243449 A1     Aug. 30, 2018

Related U.S. Application Data

(62) Division of application No. 12/520,128, filed as application No. PCT/GB2007/004944 on Dec. 21, 2007, now Pat. No. 10,441,667.

(30) Foreign Application Priority Data

Dec. 21, 2006  (GB) ...................................... 0625678

(51) Int. Cl.
   *A61K 49/00*         (2006.01)
(52) U.S. Cl.
   CPC .................................. *A61K 49/006* (2013.01)
(58) Field of Classification Search
   CPC .............................. A61P 1/02; A61K 49/006
   See application file for complete search history.

(56) References Cited

U.S. PATENT DOCUMENTS

| | | | |
|---|---|---|---|
| 4,290,433 A | 9/1981 | Alfano | |
| 5,240,697 A * | 8/1993 | Norfleet | A61K 8/19 424/49 |
| 5,409,835 A | 4/1995 | Akowicz et al. | |
| 6,769,911 B2 | 8/2004 | Buchalla et al. | |
| 7,175,430 B1 | 2/2007 | Gasser et al. | |
| 7,601,805 B2 | 10/2009 | Foti et al. | |
| 7,858,394 B2 | 12/2010 | Wunder | |
| 2003/0175807 A1 | 9/2003 | Baubert et al. | |
| 2004/0191884 A1 | 9/2004 | Isobe et al. | |
| 2005/0273867 A1 | 12/2005 | Brulet et al. | |
| 2005/0283058 A1 | 12/2005 | Choo-Smith et al. | |
| 2006/0127327 A1 * | 6/2006 | Shi | C07K 16/1267 424/50 |

FOREIGN PATENT DOCUMENTS

| | | |
|---|---|---|
| DE | 19926728 A1 | 12/2000 |
| EP | 1686379 A1 | 8/2006 |
| EP | 1700865 A1 | 9/2006 |
| GB | 2036557 A | 7/1989 |
| JP | 10236914 A | 9/1998 |
| JP | 200477217 A | 3/2004 |
| JP | 2004156017 A | 6/2004 |
| JP | 2005168463 | 6/2005 |
| WO | WO 00/71565 * | 11/2000 |
| WO | 2001/12237 A1 | 2/2001 |
| WO | 2001/92300 A2 | 12/2001 |
| WO | 200192300 A2 | 12/2001 |
| WO | 2003082904 A2 | 10/2003 |
| WO | 2005/025528 A1 | 3/2005 |
| WO | 2006010004 A2 | 1/2006 |
| WO | WO 2007/038683 * | 4/2007 |
| WO | 2007/123880 A2 | 11/2007 |
| WO | WO-2007123880 A2 * | 11/2007 ........... A61B 5/0088 |

OTHER PUBLICATIONS

Baubet et al., "Chimeric green fluorescent protein-aequorin as bioluminescent Ca21 reporters at the single-cell level", PNAS, vol. 97, No. 13, pp. 2760-7265, Jun. 20, 2020. (Year: 2020).*
Amaechi, B.T., et al., "Factors affecting the development of carious lesions in bovine teeth in vitro," Archives of Oral Biology, 1998, vol. 43, pp. 619-628, Elsevier Science Ltd.
Callan, J.F., et al., "Switching between molecular switch types by module rearrangement: Ca2+-enabled, H+-driven 'Off-On-Off', H+-driven YES and PASS 0 as well as H+, Ca2+-driven AND logic operations," Chem. Commun., 2004, pp. 2048-2049, The Royal Society of Chemistry, U.K.
Charbonneau, H., et al., "Amino Acid Sequence of the Calcium-Dependent Photoprotein Aequorin," Biochemistry, 1985, pp. 6762-6771, vol. 24, American Chemical Society, Washington, D.C.
Fagan, T.F., et al., "Cloning, expression and sequence analysis of cDNA for the Ca2+-binding photoprotein, mitrocomin," Federation of European Biochemical Societies, pp. 301-305, vol. 333, No. 3, Elsevier Science Publishers B.V.
Head, J.F., et al., "The crystal structure of the photoprotein aequorin at 2.3A resolution," Nature, May 18, 2000, pp. 372-376, vol. 405, Macmillan Magazines Ltd.
Hemingway, C.A., et al., "Enamel erosion by soft drinks with and without abrasion," British Dental Journal, Oct. 7, 2006, p. 439, vol. 201, No. 7.
Illarionov, B.A., et al., "Cloning and expression of the cDNA of the Calcium-Activated photoprotein obeline from the hydroid polypobelia longissima," Proceedings of the Academy of Sciences, Genetics, 1992, vol. 326, No. 5, UDC 575.113, Russia.
Illarionov, B.A., et al., "Sequence of the cDNA encoding the Ca2+-activated photoprotein obelin from the hydroid polyp obelia longissima," Gene, 1995, pp. 273-274, vol. 153, ElsevierScience B.V.
Inouye, S., et al., "Cloning and sequence analysis of cDNA for the Ca2+-activated photoprotein, clytin," Federation of European Biochemical Societies, 1993, pp. 343-346, vol. 315, No. 3, Elsevier Science Publishers B.V.

(Continued)

*Primary Examiner* — Lezah Roberts
(74) *Attorney, Agent, or Firm* — Ostrager Chong Flaherty & Broitman P.C.

(57) ABSTRACT

The invention relates to a method for the detection of tooth demineralisation. More specifically, the method concerns exposing a tooth to a pharmaceutical composition comprising a complex capable of producing an optical signal characteristic of the presence of free ions and detecting the resulting optical signal, and a kit for the detection of active demineralisation at tooth surfaces using such method.

22 Claims, 20 Drawing Sheets

(56) References Cited

OTHER PUBLICATIONS

Inouye, S., et al., "Cloning and sequence analysis of cDNA for the luminescent protein aequorin," Proceedings of the National Academy of Sciences USA, Biochemistry, May 1985, pp. 3154-3158, vol. 82.

Kim, T-H, et al., "A Fluorescent Self-Amplifying Wavelength-Responsive Sensory Polymer for Fluoride Ions," Angew. Chem. Int. Ed., 2003, pp. 4803-4806, vol. 42, Wiley-VCH Verlag GmbH & Co. KGaA, Weinheim, Germany.

Markova, S.V., et al., "Obelin from the Bioluminescent Marine Hydroid Obelia geniculata: Cloning, Expression, and Comparison of Some Properties with Those of Other Ca2+-Regulated Photoproteins," Biochemistry, Jan. 26, 2002, pp. 2227-2236, vol. 41, American Chemical Society, Washington, D.C.

Miyawaki, A., et al., "Fluorescent indicators for Ca2+ based on green fluorescent proteins and calmodulin," Nature, Aug. 28, 1997, pp. 882-887, vol. 388, Macmillan Publishers Ltd.

Miyawaki, A., et al., "Dynamic and quantitative Ca2+ measurements using improved cameleons," Proceedings of the National Academy of Science USA, Cell Biology, Mar. 1999, pp. 2135-2140, vol. 96.

Nagai, T., et al., "Circularly permuted green fluorescent proteins engineered to sense Ca2+," Proceedings of the National Academy of Science USA, Mar. 13, 2001, pp. 3197-3202, vol. 98, No. 6.

"Strontium and Dental Caries," Nutrition Reviews, Nov. 1983, pp. 342-344, vol. 41, No. 11.

Prasher, D., et al., "Cloning and expression of the cDNA Coding for aequorin, a Bioluminescent Calcium-Binding Protein," Biochemical and Biophysical Research Communications, Feb. 15, 1985, pp. 1259-1268, vol. 126, No. 3, Academic Press, Inc.

Prasher, D., et al., "Sequence Comparisons of Complementary DNAs Encoding Aequorin Isotypes," Biochemistry, 1987, pp. 1326-1332, vol. 26, American Chemical Society, Washington, D.C.

Rawls, H.R., et al., "Demonstration of Dye-Uptake as a Potential Aid in Early Diagnosis of Incipient Caries," Caries Res., 1978, pp. 69-75, vol. 12.

Rudolf, R., et al., "Looking forward to seeing calcium," Nature Reviews, Molecular Cell Biology, Jul. 2003, pp. 579-586, vol. 4.

Shimomura, O., et al., "Halistaurin, phialidin and modified forms of aequorin as Ca2+ indicator in biological systems," Biochem. J., 1985, pp. 745-749, vol. 228, Great Britain.

Shimomura, O., "The discovery of aequorin and green fluoroscent protein," Journal of Microscopy, Jan. 2005, pp. 3-15, vol. 217, Pt. 1, The Royal Microscopical Society.

Shimomura, O., et al., "Peroxidized coelenterazine, the active group in the photoprotein aequorin," Proceedings of the National Academy of Science USA, Biochemistry, Jun. 1978, pp. 2611-2615, vol. 75, No. 6.

Thorpe, J.H., et al., "Conformational and Hydration Effects of Site-Selective Sodium, Calcium and Strontium Ion Binding to the DNA Holliday Junction Structure d(TCGGTACCGA)4," Journal of Molecular Biology, 2003, pp. 97-109, vol. 327, Elsevier Science Ltd.

Tsuji, F.I., et al., "Molecular evolution of the Ca2+-binding photoproteins of the hydrozoa," Photochemistry and Photobiology, 1995, pp. 657-661, vol. 62, No. 4, American Society for Photobiology, United States.

Ward, W.W., et al., "Properties of Mnemiopsin and Berovin, Calcium-Activated Photoproteins from the Ctenophores *Mnemiopsis* sp. and *Beroe ovata*," Biochemistry, 1974, pp. 1500-1510, vol. 13, No. 7.

Chinese Equivalent Application 200780051625.9 Rejection Decision dated May 23, 2013 and English translation.

Hay, DI et al., "Equilibrium dialysis and ultrafiltration studies of calcium and phosphate binding by human salivary proteins. Implications for salivary supersaturation with respect to calcium phosphate salts" Calcif Tissue Int. 1982; 34(6):531-8 (Abstract Only) cited in response to CN rejection.

Esser, D. et al., Sample Stability and Protein Composition of Saliva: Implications for Its Use as a Diagnostic Fluid Biomarker Insights 2008:3 25-37.

Material Safety Data Sheet—BAPTA—cited in response to Chinese rejection.

Zhong, F. et al., "Bcl-2 differentially regulates Ca 2+ signals according to the strength of T cell receptor activation" Journal of Cell Biology 2006: 172(1) 127-137.

Gorokhovatsky, AY et al., "Fusion of Aequorea victoria GFP and aequorin provides their Ca2+-induced interaction that results in red shift of GFP absorption and efficient bioluminescense energy transfer" J. Biochemical and Biophysical Research Communications 2004: 320 703-711.

Translation of Office Action prepared dated Jun. 14, 2012 for corresponding Japanese patent application, No. JP2009-542225.

Translation of second Office Action dated Sep. 13, 2012 for corresponding Chinese patent application, No. 2007800516259.

Stepanyuk, Galina A., et al., "Interchange of aequorin and obelin bioluminescence color is determined by substitution of one active site residue of each photoprotein," FEBS Letters, 2005, pp. 1008-1014, vol. 579, Federation of European Biochemical Societies, Published by Elsevier B.V.

\* cited by examiner

Figure 2 shows an example image of a tooth with a 'window' as demarked by nail varnish and to which the gel was applied. Image taken in the light.

Figure 3 depicts images showing the light output from window, following incubation in gel (either pH 4.7 or 6.4), rinsing and addition of disclosing gel. Brighter areas indicate regions of more light and correspond to regions where free calcium is present.

Figure 4 shows a graph depicting the light output from acid- or neutral-gel treated teeth. Acid pH 4.67; control pH 6.4. 'Brightness' was determined using the "plot profile" function of ImageJ.

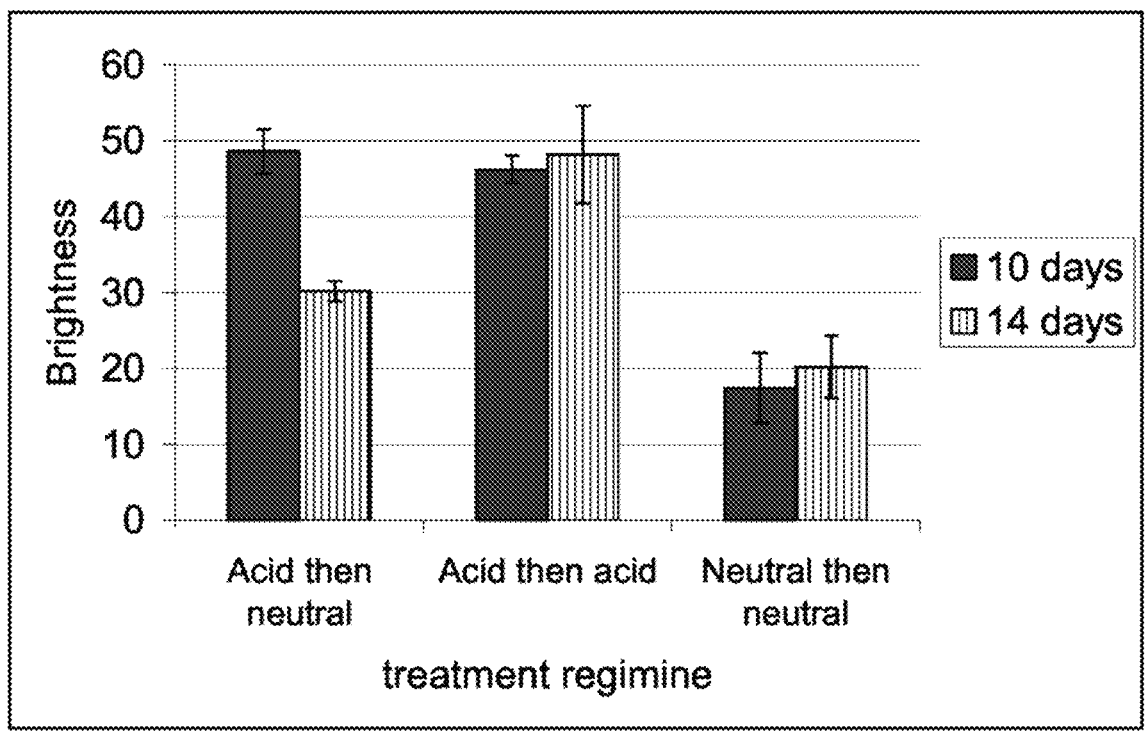
FIG. 5
Figure 5 shows a graph depicting light output from acid- or neutral-gel treated teeth. Teeth were first incubated in gel (acid pH 4.67, or neutral pH 6.4) for 14 days before brightness was assessed and the teeth were transferred to new gel with pH 4.67 or 6.4. 'Brightness' was determined using the "plot profile" function of ImageJ.
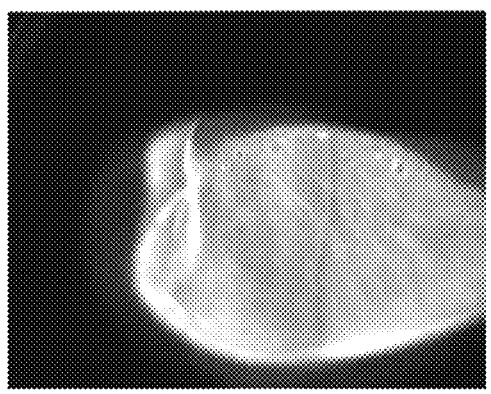
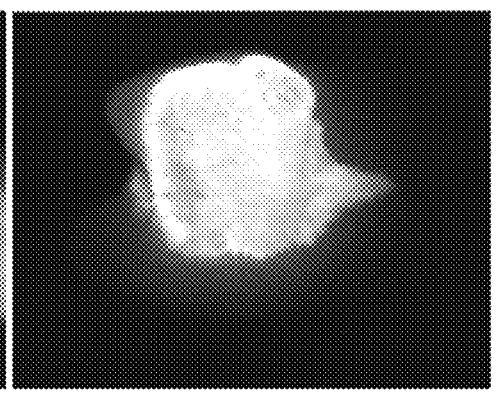
FIG. 6A  FIG. 6B Figure 12 showing deciduous molars with cavitated lesions (A). (a and c) images of the teeth in the light (b and d) monochromatic image following application of disclosing gel.

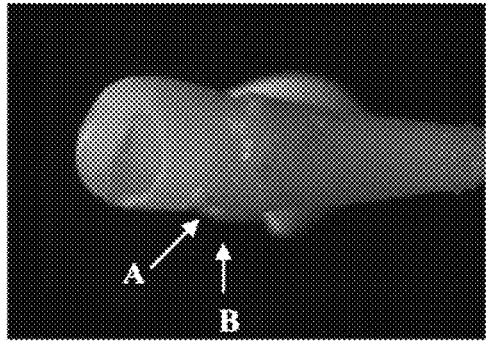 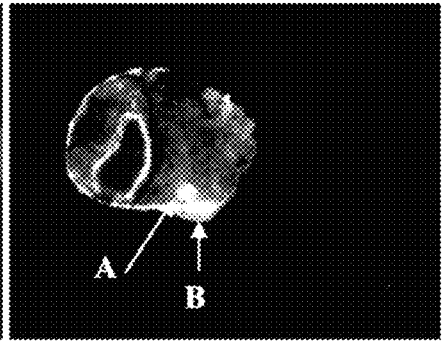

FIG. 13A　　　　　　　FIG. 13B

Figure 13 shows an incisor (deciduous) with a large caries lesion (known as nursing bottle syndrome). (a) image of the tooth in the light (b) monochromatic image following application of disclosing gel. The expected region of activity was around the edge of the lesion where demineralization is likely. This was corroborated by regions of greatest light from the edge of the lesion. High light is also observed at spot A, where the dentist caused disruption of the tooth surface during extraction. Some background from mounting material is also observed (B).

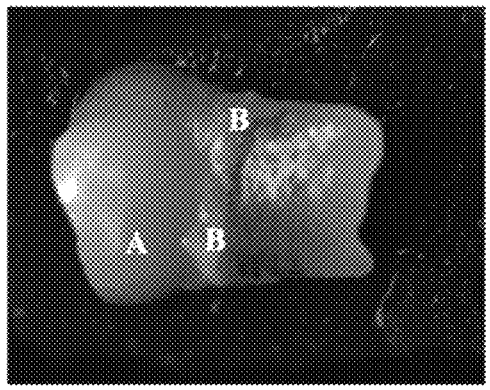 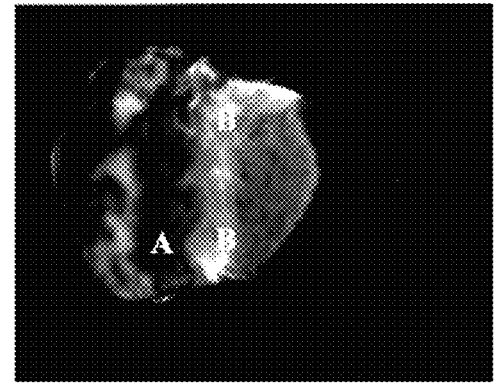

FIG. 14A　　　　　　　FIG. 14B

Figure 14. Image showing the smooth surface of a molar (deciduous). (a) image of the tooth in the light (b) monochromatic image following application of disclosing gel. A whitespot lesion (A) is visible as is residual gingival tissue (B). The assay shows a distinctive patterning, similar to the white spot lesion.

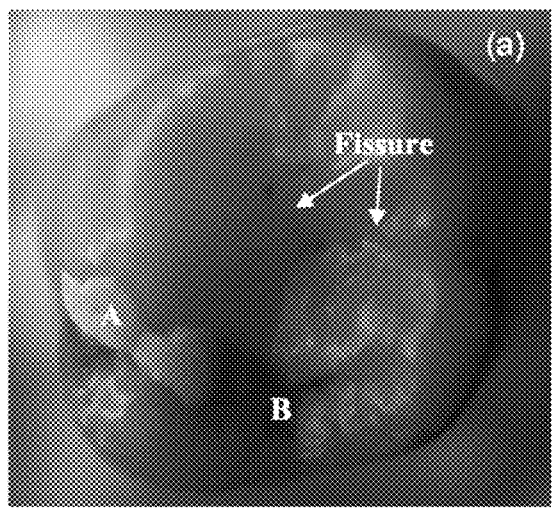 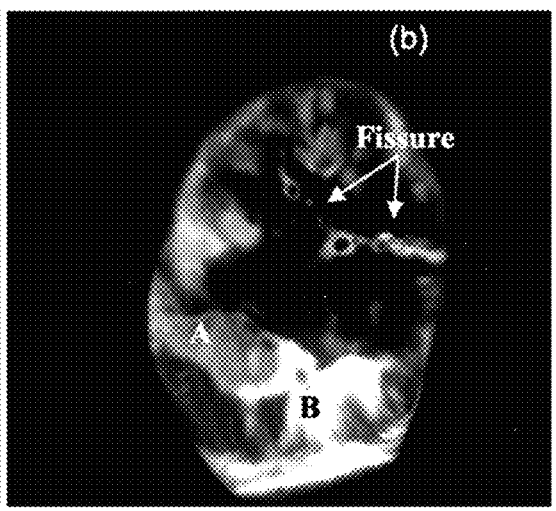

FIG. 15A　　　　　　　　FIG. 15B

Figure 15 showing images of the occlusal surface of molar (permanent). (a) image of the tooth in the light (b) monochromatic image following application of disclosing gel. A resin filling is evident at position A. Before addition of disclosing gel a dentist predicted active caries at position B and suggested that active caries lesions may also be present in the fissures of the tooth. Our assay indicates large amounts of light and thus active demineralization from position B as well as light captured from the fissures. Note the differences in the size of images 9a and 9b indicating that the disclosing gel did not cover the full occlusal surface.

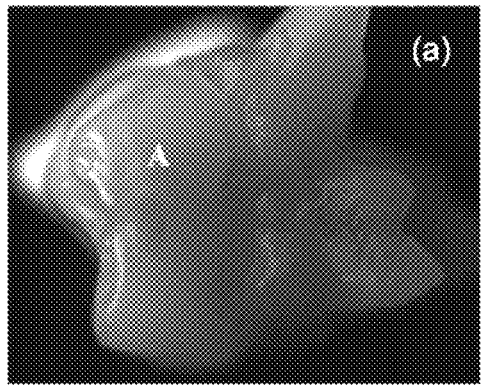
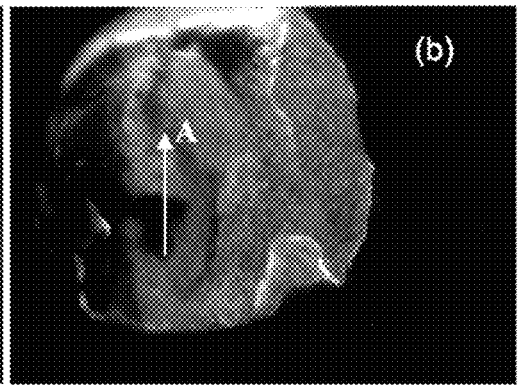

FIG. 16A    FIG. 16B

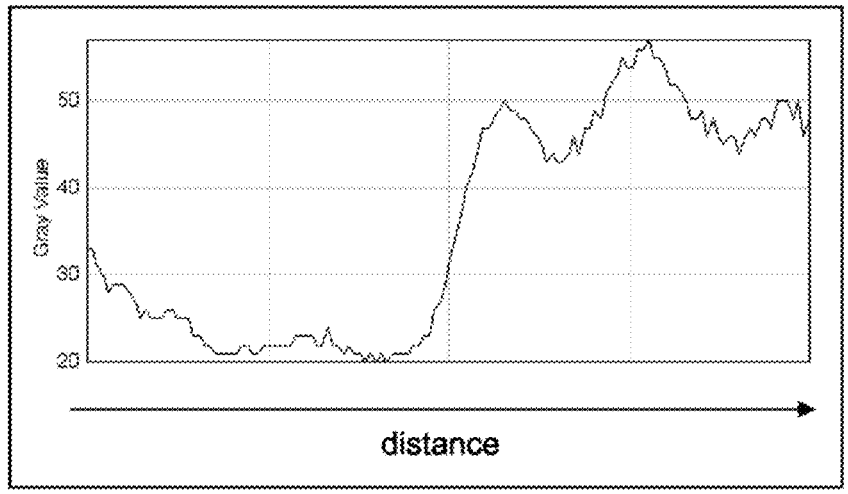

FIG. 16C

Figure 16 showing a molar (deciduous). (a) image of the tooth in the light (b) monochromatic image following application of disclosing gel (c) graphical representation of the light generated across lesion ( →  ). A whitespot lesion (A) is visible. Before addition of disclosing gel a dentist predicted indicated that the whitespot was faceted across the surface, with remineralisation in the lower region. We observed distinctive patterning from the faceted lesion with a strong signal from the upper area of the whitespot lesion and less light from the lower, remineralised region of the tooth. This provides evidence that the assay can be used to assess the activity of a caries lesion and can differentiate between active and inactive lesions.

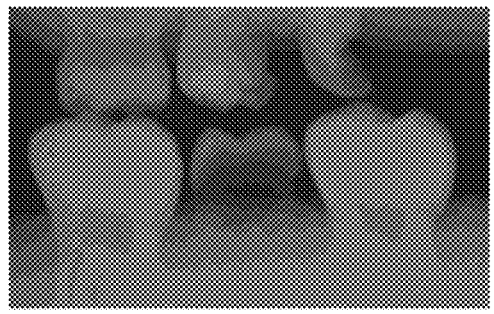

FIG. 17A

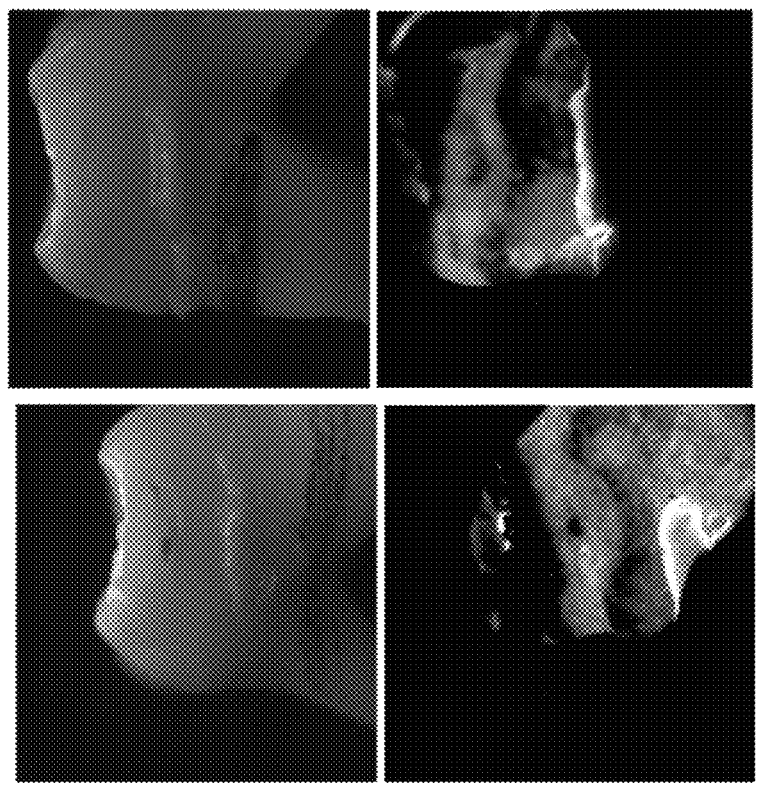

FIG. 17B

Figure 17a shows an x-ray of permanent molars whose mesial surface was also investigated with disclosing gel (17b). The mesial surfaces of the teeth are to the left in the x-ray, it is clear that no demineralization, which would be visible as a dark shadow, is present in either of the permanent molars although regions of active demineralization were observed using disclosing gel (17b, images on left are taken in the light and on the right monochromatic images after addition of disclosing composition). The approach is therefore capable of identifying an active lesion long before an x-ray is capable of detecting demineralisation at these sites.

Figure 18 (a) shows an image of a tooth that had been rinsed in deionised water and removed before being assessed (b) shows a tooth that had been rinsed and assessed in saliva (c) shows a tooth that had been rinsed in saliva but removed before being assessed (d) shows a tooth that had been incubated in saliva, removed, rinsed in deionised water before being assessed.

Figure 19 shows (a) Supra-gingival calculus and (b) sub-gingival calculus and were imaged following addition of disclosing solution.

Figure 20 shows (a) image of the tooth in the light (b) monochromatic image following application of disclosing gel. Box indicates area of calculus.

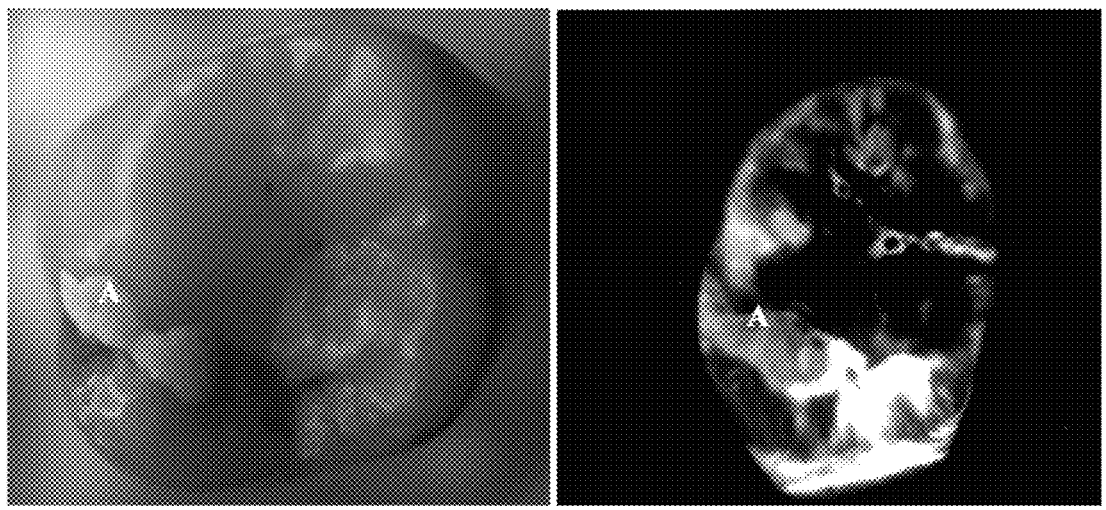

FIG. 21

Figure 21. Images shows the occlusal surface of molar (permanent). (a) image of the tooth in the light (b) monochromatic image following application of disclosing gel. A resin filling is evident at position A. Limited amounts of light were present from the resin (A), suggesting interferences from similar resin fillings is expected to be minimal. Note the differences in the size of images 21a and 21b indicating that the disclosing gel did not cover the full occlusal surface.

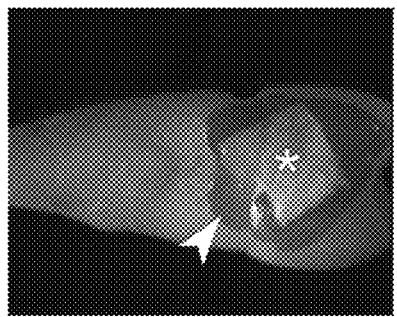 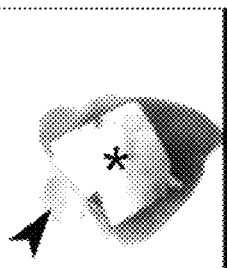 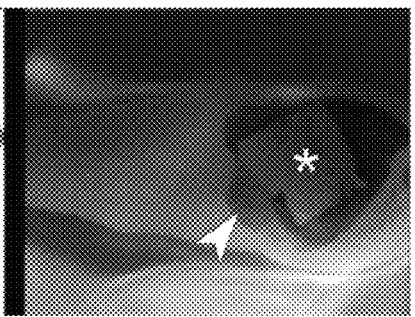
FIG. 25A     FIG. 25B     FIG. 25C
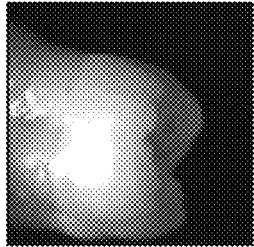 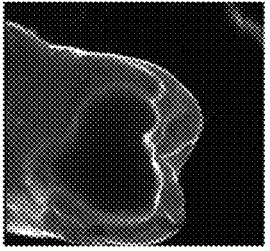 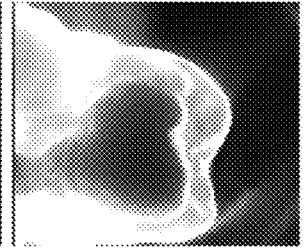 
FIG. 26A     FIG. 26B     FIG. 26C     FIG. 26D

COMPOSITION AND METHOD FOR DETECTION OF DEMINERALISATION

RELATED APPLICATION

This application is a divisional of and claims priority from U.S. patent application Ser. No. 12/520,128 having a 371(c) date of Jul. 23, 2009, which is the U.S. national stage application under 371 of International Application No. PCT/GB2007/004944 filed Dec. 21, 2007, claiming priority to Great Britain Patent Application No. 0625678.8 filed on Dec. 21, 2006.

TECHNICAL FIELD

The invention relates to a composition for the detection of tooth demineralisation. More specifically, the invention concerns a composition comprising a complex capable of producing an optical signal characteristic of the presence of free ions, the pharmaceutical uses of such a composition, and methods and a kit for the detection of active demineralisation at tooth surfaces using such a composition.

BACKGROUND

Tooth enamel contains large crystals of apatite, which form a tightly packed structure; however tiny intercrystalline spaces or pores, which are filled with water and organic material, separate the crystals. The form of apatite found in teeth is hydroxyapatite, the smallest repeating unit of which is $Ca_{10}(PO_4)_6.2(OH)$. The components of the crystal can be substituted. Known substituents include strontium, barium, lead, sodium, potassium and magnesium for calcium; the halogens (F, Cl, I, Br) for hydroxide and carbonate; and hydrogen phosphate for phosphate. Of these substitutions fluoride and carbonate are reported to be the most important, with fluoride preventing/repairing caries and carbonate increasing susceptibility to caries. Many other ions such as zinc, tin and iron are also reportedly found in surface enamel. The organic material (1% by weight, 2% by volume) found in fully formed enamel mainly consists of enamelins (mass 50-70 kDa), but also contains low molecular weight lipids, and some carbohydrate and organic acids such as citrate and lactate. Enamelins can be detected by immunoblot analysis.

Many dental problems result from tooth demineralisation. Demineralisation is an underlying process involved in the development of dental caries, tooth erosion and dentine hypersensitivity. Demineralisation of one or more of the dental hard tissues causes a loss of tooth integrity. Minerals are generally present in the dental hard tissues in a mineralised state and demineralisation involves the release of free ions.

Dental caries lesions damage the structure of teeth. The disease dental caries can lead to pain, infection, bad breath, foul tastes and tooth loss. In severe cases, infection can spread to the surrounding soft tissues, which can result in death. Factors inducing caries include bacteria, which collect around teeth in a sticky mass known as plaque, and ingested food and drink. The bacteria associated with early demineralisation are *Streptococcus mutans*, while lactobacilli appear to be related to lesion progression. These bacteria convert sugars in food/drink into acids, such as lactic acid, through fermentation, and, if left in contact with teeth, these acids cause demineralisation. This removal of mineral from the crystal surface of teeth makes the structure more porous and susceptible to attack. As the pores increase in size, acid can penetrate deeper into the tissue and dissolve subsurface minerals. Demineralisation is eventually followed by disintegration of the organic material. If this is allowed to progress, mineral content is lost to the extent that soft organic material left behind disintegrates forming a cavity or break in the surface integrity of the tooth. The presence of the plaque biofilm at the surface is essential if caries is to progress.

Technologies exist to determine the location and extent (depth and/or volume mineral loss) of caries lesions. Identifying regions of demineralization is currently used by clinicians to detect caries and other dental problems. This may involve visual examination by a clinician, radiography or state of the art technologies such as DIAGNOdent (patent number U.S. Pat. No. 4,290,433). Employing visual inspection to detect caries relies on the skill of the assessor and more importantly the extent of demineralisation/erosion. Often significant damage will have occurred by the time caries are detected this way. X-ray analysis can reveal the presence of caries invisible to the eye however ongoing assessment is needed to determine caries activity. State of the art technologies that can aid in caries diagnosis include fibre optic illumination with light or lasers. DIAGNOdent (U.S. Pat. No. 4,290,433) and Quantitative Light-induced Fluorescence (QLF) (U.S. Pat. No. 4,290,433) involve illuminating the tooth surface with red laser light (633 nm) or high intensity blue light respectively and then analysing the emitted fluorescence. The nature of the emitted fluorescence can be correlated with the degree of demineralisation in the tooth. Other methods such as the ultrasonic caries detector (UCD) employ ultrasonic waves (US2007238996) to create an image of the tooth, where the level of reflectance is proportional to the density of the tissue; or Raman spectroscopy (US2005283058) which is sensitive to mineral and crystal orientation to characterise the enamel surface.

Dental erosion is a progressive loss of hard tissue thickness incrementally from the tooth surface and is frequently caused by acidic drinks/foods (which may or may not be sugary), which cause demineralisation and can lead to exposure of the dentine. Erosion can also be accelerated by tooth-brushing of acid-softened enamel (or dentine), leading to the complete removal of enamel and consequent exposure of dentine. Specifically, erosion refers to non-bacterial processes causing progressive loss of hard dental tissue. Tooth erosion occurs when the enamel on your teeth is worn away by acid. Usually the calcium contained in saliva will help remineralise (or strengthen) your teeth after you consume small amounts of acid, but the presence of a lot of acid in your mouth does not allow for remineralisation. Acid can come from many sources, including carbonated drinks. All "fizzy" drinks contain acid and can dissolve enamel very quickly. Increasing quantity consumed leads to increased damage as does holding the drink in the mouth for longer times. Pure fruit juice contains acid and therefore acts in a similar way to carbonated drinks. Bulimia and acid reflux can contribute to tooth erosion due to the exposure of teeth to stomach acids.

There are a number of signs of tooth erosion, ranging from its early stages (sensitivity, discoloration, rounded teeth) to the later, more severe stages (cracks, severe sensitivity, cupping). Wearing away of protective enamel leads to increased exposure of nerve endings in dental pulp leading to pain when you consume hot, cold, or sweet foods and drinks. The patient may therefore often present with sensitivity. Severe sensitivity may develop as more enamel is worn away and teeth become increasingly sensitive. Patients may also present with discoloured teeth, as they can become slightly yellow when the dentin is exposed. Teeth may have a rounded or "sand-blasted" look as a result of erosion. Front teeth may appear slightly transparent near the biting edges. Advanced discoloration may result—teeth may become more yellow as more dentin is exposed because of the loss of tooth enamel. Small cracks and roughness may appear at the edges of teeth, and cupping may occur as small dents may appear on the chewing surface of the teeth. Fillings also might appear to be rising up out of the tooth. If tooth erosion can be identified early, then treatment can be applied and teeth protected. For example, problem areas may be sealed to prevent further demineralisation. Early detection and diagnosis are therefore paramount.

Dentine hypersensitivity is the pain arising from exposed dentine, typically in response to external stimuli (and which cannot be explained by any other form of dental disease). The exposed open dentinal tubules lead directly to pulp tissues, which include the nerves within it. When the cementum covering root dentine is no longer present (due to erosion or abrasion) after the gums have receded, tubules are exposed and sensitivity and pain can occur. In cases of hypersensitivity, the dentine has up to 8 times more tubules open at the dentine surface and the tubule diameter is wider than when no pain is present. This provides a greater available surface area for demineralisation, such as by acidic drinks and also leads to the release of more calcium following application of such products.

As mentioned above, the development of caries, erosion or hypersensitivity is caused by a loss of tooth integrity through demineralisation of one or more of the dental hard tissues. Hydroxyapatite, the main component of enamel becomes soluble when exposed to acidic environments. Teeth are under constant attack from their external environment. Plaque bacteria on the tooth surface produce acids and after sugary meals or snacks, the acidity of the plaque can increase dramatically. During exposure to any acidic environment, portions of inorganic material content at the surface of the teeth dissolve and can remain dissolved for over 2 hours. Acid can permeate the microscopic pores created by this surface demineralisation and a sub-surface demineralised layer within the tooth can be created as the surface layer partially remineralises as the plaque acidity returns to lower levels. Oscillating periods of demineralisation and remineralisation are therefore a "normal" feature at the surface of teeth in the presence of plaque.

Dentine and cementum are more susceptible to acid demineralisation than enamel, as they have a lower mineral content. The caries process is a dynamic one which starts at the surface of a tooth, but due to complex demineralisation-remineralisation processes related to mineral concentration gradients in the fluid within the tooth and plaque, the surface becomes more highly mineralised than the sub-surface region. Substitution readily occurs in the inorganic structure of enamel, and so demineralisation also results in the release of many different ions. This factor is especially important for early detection, as the enamel surface is the location of initial uptake and is also the very first point of acid attack.

Common substituents include sodium, magnesium, fluoride and carbonate. Magnesium and carbonate can penetrate into enamel and are known to change the crystal structure of apatite so that it becomes more soluble; therefore these ions are preferentially lost from the subsurface upon acid attack. Higher concentrations of zinc, lead, tin and iron are also found in surface enamel compared with deeper layers. Analysis of carious lesions in enamel usually shows high levels of fluoride together with appreciable levels of magnesium, which is believed to be due to the rapid uptake of these ions by the newly exposed layers of apatite.

Although some technologies exist to determine the location and extent (depth and/or volume mineral loss) of caries lesions, a major drawback of these methods is that they do not address the nature of the caries process i.e. if they are active or inactive at any one specific point in time. Inactive caries lesions may not require treatment, whereas active caries lesions will (by definition) indicate ongoing demineralisation. It would also be beneficial to have information about demineralisation as early as possible. Often active caries will remain undetected until late in the process and significant damage has been done to the integrity of the tooth. Sometimes it is only when the patient starts to feel pain that an X-ray is used to confirm the presence of caries. Currently, the active nature of the caries can only be determined by assessing progress of the caries lesion over time, typically during a period of more than a year in the case of radiographs (X-rays). If caries, tooth erosion or hypersensitive teeth can be identified early, then treatment can be applied and teeth protected. For example, problem areas may be sealed to prevent further demineralisation. Early detection and diagnosis are therefore paramount. Further, it is preferable that information about activity is captured in one examination.

Initial caries diagnosis involves inspection of all visible tooth surfaces, often using a dental explorer, or metal pick, and mirror, illuminated by a bright light source. In some cases, the sign of a carious lesion or of demineralisation of enamel is the appearance of a chalky white spot on the surface of a tooth. However such a spot is not always visible.

A common technique to diagnose early caries is to blow air across the suspect surface. The resulting loss of moisture from the surface changes the optical properties of the demineralised enamel, allowing visualisation of a white spot lesion indicative of early caries. As it continues to demineralise, caries may turn brown and eventually develop into a cavity. Large caries lesions are often visible to the naked eye. However, smaller lesions can be very difficult to identify. Once a cavity forms, the lost tooth structure cannot be regenerated. The process before this point is potentially reversible, therefore it is essential to identify caries as soon as possible.

State of the art technologies that can aid in caries diagnosis include fibre optic illumination with light or lasers. Diagnodent is a technology covered by U.S. Pat. No. 6,769,911, whereby a tool containing a probe element and an integrated red light source induces fluorescence in the bacterially-infected carious region of a tooth, which after passing through an appropriate filter, is measured by the device. However, this method provides no indication as to whether the caries is active or inactive.

Dyes, including fluorescent dyes, have also been used to identify the location of bacteria and presence of acid on teeth as a method to detect tooth decay. However, these dyes tend to be toxic and so are inappropriate for in-mouth analysis. Furthermore, enamel is auto-fluorescent and so background fluorescence can be prohibitively high.

Erosion is detected by visual inspection, as for caries detection. Signs and symptoms that indicate erosion include increased transparency of incisors, fillings raised above the surrounding teeth, and wear on non-biting surfaces. These all take time to develop to a visible degree, and the damage will already have been done. It would be desirable to have a method for testing demineralisation as a result of erosion, for a number of reasons. For example, certain foods or drinks could be applied to teeth, followed by the disclosing composition. The disclosing composition would emit a detectable signal if ions were being emitted as a result of the food or drink being in contact with the tooth. A manufacturer to determine how potentially damaging an edible product could be to teeth could use this test, either to measure standard food or drink products, or in the development of tooth-friendly products (low potential to cause erosion) or erosion prevention products such as toothpastes and sealants. A dental clinician may also use the disclosing composition to determine a patient's susceptibility to erosion and as determined by tooth composition and saliva.

Dentine hypersensitivity will be reported by the patient and investigated by a dentist. Useful diagnostic tools are the air/water syringe, dental explorer, percussion testing, bite stress tests, and other thermal tests such as an ice cube and assessment of occlusion. However, these methods, based on the patient's report, are subjective and lack accuracy.

SUMMARY

It is an object of the invention to mitigate problems such as those described above.

According to a first aspect of the invention, there is provided a pharmaceutical composition comprising a complex capable of producing an optical signal characteristic of the presence of free ions.

According to a second aspect of the invention there is provided a composition for use in detecting active dental caries and/or active tooth demineralisation due to erosion, comprising a complex capable of producing an optical signal characteristic of the presence of free ions.

The complex for detection may be a dye, synthetic ion chelator such as an EDTA-reporter complex or a macrocycle such as a crown ether reporter complex, a protein or protein-reporter complex, a molecular imprinted polymer-reporter complex or molecular probe such as Holliday junction. One or a combination of these complexes may be used, for example if different ions are to be detected.

The ions to be detected may comprise calcium ions, magnesium ions phosphate ions, carbonate ions, potassium ions, strontium ions, fluoride ions copper ions, chloride ions, zinc ions, lead ions, tin ions, iron ions or organic material such as enamelins. Detection of different ions may help to determine the location of demineralisation and its depth into the dental hard tissues, because, as described herein, different ions may be present in different dental hard tissues.

The composition may further comprise a pharmaceutically acceptable additive and the additive is preferably a bactericidal or bacteriostatic agent.

The composition may comprise a pharmaceutically acceptable excipient and the excipient is preferably a flavouring or colouring additive.

It is preferred that the composition is in a pharmaceutically acceptable dosage form and the composition is preferably a liquid, a powder or a gel. The composition may comprise from 1 ng/ml to 10 mg/ml complex, or any concentration that gives a significantly high signal to noise ratio.

The composition may comprise a protein or a protein complex. Such a complex may undergo a conformational change on binding free ions that leads to an optical signal being generated.

It is preferred that the protein or protein complex comprises aequorin, obelin, clytin, mitrocomin, halistaurin, phialidin, mnemiopsin, symplectin, gr-bolinopsin, casein, calsequestrin, calexcitin, calcium binding cysteine protease, calmodulin and other EF hand proteinsor berovin. The person skilled in the art would be aware of other proteins or protein complexes that are functionally similar and which could be selected without undue effort.

It is preferred that the protein or protein complex comprises tandem fusions of fluorescent proteins and ion binding proteins such as calmodulin, a calmodulin-binding peptide (M13), and an enhanced green- or yellow-emitting fluorescent protein.

As an alternative, the complex may fluoresce at a characteristic wavelength indicative of the presence of ions.

The composition may comprise both a protein or protein complex which produces an optical signal on binding with free ions, and a protein or protein complex which fluoresces at a characteristic wavelength indicative of the presence of ions.

These may be modified, for example by altering the DNA sequence of the gene, by acetylation, ethoxycarbonylation, fluorescamine-modification or fluorescein labelling or by creation of chimeric proteins such as a GFP-aequorin (US2003175807) to enhance the signal, prolong the duration of signal or alter its emission spectra. Proteins and protein complexes with similar function, such as those undergoing a conformation change on binding an ion that leads to an optical signal may also be used.

The protein or protein complex preferably comprises a recombinant protein (expressed to a high purity). The protein or protein-protein complex may be administered in a solution free of the specific ion in order to reduce background signal. This may be achieved using an ion chelator.

Preferably, the composition will be optically transparent. This will allow the composition to transmit light emitted on contact of the ion-sensitive reporter with the free ions. Additives may also be added to alter the signal for example, a gel to extend the length of time that the detectable signal remains detectable, buffers to optimise the reaction or modified substrate to prevent immediate flash, but which can be triggered later such as the Enduren system for coelenterate luciferases.

The optical signal produced by the composition on exposure to free ions may be detected by a spectrophotometer, charge coupled device (CCD), complementary metal-oxide semiconductor CMOS, digital camera, intensified camera, intraoral camera, videoscope, photographic film, fibre-optic device, photometric detector, photomultiplier, micro-electro-mechanical system (MEMS) or visually by eye.

According to a third aspect of the invention, there is provided the use of a pharmaceutical composition as described above for the manufacture of a preparation for the detection of dental caries. Active dental caries can be differentiated from inactive dental caries, on the basis of the presence of demineralisation, the composition may therefore be used in the manufacture of a preparation for use in the differentiation between active and inactive dental caries.

According to a fourth aspect of the invention, there is provided the use of a pharmaceutical composition as described above for the manufacture of a preparation for the detection of active tooth demineralisation due to erosion.

According to a fifth aspect of the invention, there is provided the use of a pharmaceutical composition as described above for the manufacture of a preparation for the detection of sites of dentine demineralisation related to dentine hypersensitivity.

According to a sixth aspect of the invention, there is provided a method for the detection of active tooth demineralisation, comprising the steps of exposing a tooth to a composition as described hereinabove; and detecting the resulting optical signal.

The method may include the additional step of marking regions of the tooth or tooth model in order to allow identification of particular regions of the tooth or tooth model. It can be difficult to ensure that the same area of a tooth or tooth model can be monitored and may aid future analysis such as when comparing data from different techniques or for monitoring progression of a disease or treatment over time. Such a mark may be made with dye, pencil or by attaching a grid, such as that made out of copper wire to the tooth, such as with nail varnish.

The method may further comprise the step of exposing the tooth to a sensitising solution prior to exposure with the composition. The sensitising solution may be an acidic or a sugary (where plaque is present) solution. This may allow the susceptibility of the tooth to erosion to be determined. This could be used in order to assess an individual's susceptibility to tooth erosion. This method could also be used to assess the dental erosive properties of food or drink products.

The method may further comprise the step of allowing a period of time to lapse in between applying the sensitising solution and applying the detection composition. This is to allow the saliva in the mouth to build up, and allows the user to assess the protective effect of the saliva. This period of time may be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 seconds but may be any other time deemed necessary in order to allow the saliva to return to its normal volume and composition in the mouth, for example, a minute, two minutes or up to five minutes may be required. The length of time required will depend on the volume and the flow of saliva in the individual patient and can easily be determined by the person skilled in the art.

The optical signal may be detected by means of a spectrophotometer, charge coupled device (CCD), complementary metal-oxide semiconductor CMOS, digital camera, intensified camera, intraoral camera, videoscope, photographic film, fibre-optic device, photometric detector, photomultiplier, avalanche photodiode, light sensitive array, micro-electro-mechanical system (MEMS) or visually by eye.

According to a seventh embodiment of the invention, there is provided a kit for use in detecting demineralisation, comprising a composition comprising an ion-sensitive complex, means for applying the composition and a detector unit. The kit may also include an acidic or sugary sensitising solution. The kit may further include a marker such as a grid for marking areas of interest on a tooth or tooth model. The kit could be purchased, for a number of reasons. A dentist may wish to have a convenient commercially available test kit for use in assessing a patient's susceptibility to erosion. A home-use test of erosion susceptibility could be used by a consumer, who could then decide what preventative measures to take. Manufacturers of food or drink products could purchase the test if the tooth-eroding properties of their products are of interest.

Thus, the invention seeks to provide a composition and a method using such a composition for the detection of free ions in dental applications.

BRIEF DESCRIPTION OF THE DRAWINGS

The invention will be further described by way of example only and with reference to the accompanying figures in which:

FIGS. 4 and 5 demonstrate the use of an image analysis programme ImageJ to determine the brightness of the area treated with acid gel and disclosing gel;

FIGS. 6A to 6B demonstrate the use of obelin as a disclosing composition;

FIG. 12, panels (a) and (c), show images of the teeth in the light and FIG. 12, panels (b) and (d) show monochromatic image following application of disclosing gel;

FIG. 13A shows an incisor (deciduous) with a large caries lesion (known as nursing bottle syndrome), the image of the tooth taken in the light;

FIG. 13B monochromatic image of an incisor (deciduous) with a large caries lesion (known as nursing bottle syndrome) following application of disclosing gel;

FIG. 14A is an image showing the smooth surface of a molar (deciduous), the image of the tooth in the light;

FIG. 14B is a monochromatic image showing the smooth surface of a molar (deciduous) following application of disclosing gel;

FIGS. 15A and 15B shows images of the occlusal surface of molar (permanent). FIG. 15A shows an image of the tooth in the light FIG. 15B shows a monochromatic image following application of disclosing gel;

FIG. 16A is an image of a molar (deciduous) taken in the light;

FIG. 16B shows a monochromatic image following application of disclosing gel;

FIG. 16C is a graphical representation of the light generated across a lesion;

FIG. 17A shows an x-ray of permanent molars;

FIG. 17B shows permanent molars whose mesial surface was also investigated with x-ray then disclosing gel;

FIG. 18, panel (b), shows a tooth that had been rinsed and assessed in saliva; FIG. 18, panel (c), shows a tooth that had been rinsed in saliva but removed before being assessed;

FIG. 18, panel (d), shows a tooth that had been incubated in saliva, removed, and rinsed in deionised water before being assessed;

FIG. 19, panel (b), shows sub-gingival calculus and imaged following addition of disclosing solution;

FIG. 20, panel (b), shows a monochromatic image following application of disclosing gel; box indicates area of calculus;

FIG. 21, the left hand panel, shows images of the occlusal surface of molar (permanent) in the light prior to application of disclosing gel;

FIG. 21, the right hand panel, monochromatic image of the occlusal surface of molar (permanent) following application of disclosing gel;

FIGS. 25A to 25C show the results of experiments carried out using acid etched teeth;

FIGS. 26A to 26D show the results of further experiments carried out using acid etched teeth;

DETAILED DESCRIPTION

Figure 1:
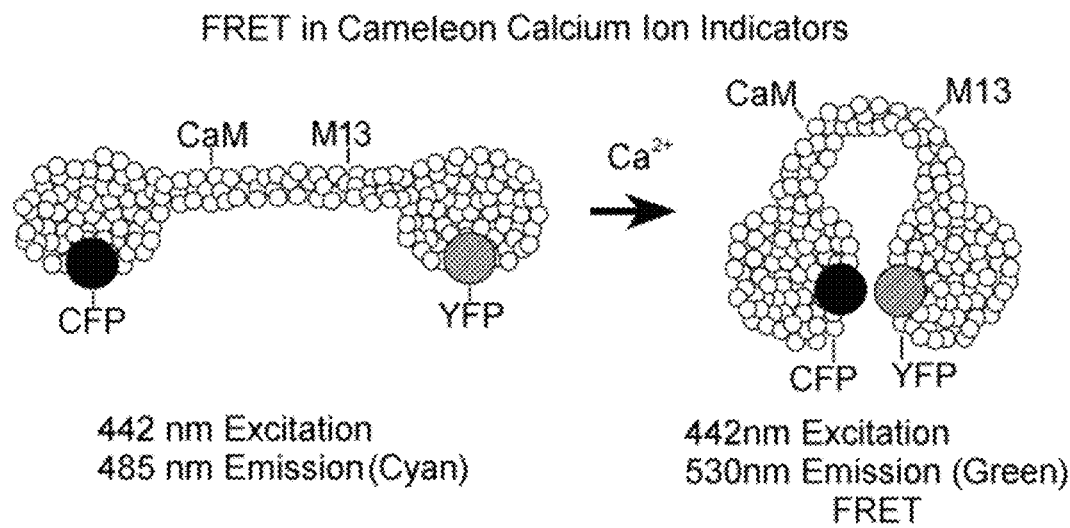
FIG. 1 is a schematic representation of FRET in cameleon indicators.

In the context of the invention, an "ion-sensitive complex" means a complex capable of producing an optical signal characteristic of the presence of free ions released as a result of demineralisation. The complex may be a dye, synthetic ion chelator such as an EDTA-reporter complex or a macrocycle such as a crown ether reporter complex, a protein or protein-reporter complex, a molecular imprinted polymer-reporter complex or Holliday junction. which may be modified to increase sensitivity to ions, to improve signal strength, to prolong signal, to improve signal to noise, to improve spectral response. Recombinant or modified protein may also be used.

The invention concerns the novel pharmaceutical use of one or a combination of ion-sensitive dyes, synthetic ion chelators such as an EDTA-reporter complexes or macrocycles such as a crown ether reporter complexes, protein or protein-reporter complexes, molecular imprinted polymer-reporter complexes or molecular probes such as Holliday junctions as reporters in the detection of dental demineralisation. As discussed above, the presence of free ions at the tooth surface indicates the presence of demineralisation. These reporters can be used to detect the presence of free ions on teeth, thus helping to detect specific dental problems.

In the presence of free ions, an optical signal is emitted from the ion-sensitive reporter. The spectra, intensity or duration of the signal is proportional to the quantity of free ions. Different tissues have different amounts and types of ions available and so the response to the ion-sensitive reporters will vary between tissues. In the process of dental erosion dentine may eventually be exposed. In the process of dentine hypersensitivity, cementum is removed and root dentine is exposed. Dentine and cementum are less mineralised than enamel and thus respond directly to the ion-sensitive reporters. These demineralised features of teeth may be identified by areas having more intense optical signals.

In the presence of active caries, free ions will continue to be released as the tooth is demineralised by the acidic environment and bacteria. The localisation and intensity of this signal allow the localisation of the active caries to be determined.

The composition may contain one or more of the following: dye, synthetic ion chelator such as an EDTA-reporter complex or a macrocycle such as a crown ether reporter complex, a protein or protein-reporter complex, a molecular imprinted polymer-reporter complex or molecular probe such as Holliday junction. The protein or protein complex may include ion sensitive photoproteins, ion sensitive fluorescent proteins, or protein complexes detectable by fluorescence, bioluminescence, chemiluminescence or fluorescence resonance energy transfer (BRET, CRET or FRET)), labelled antibodies which recognize organic material e.g. enamelins The synthetic ion chelator or protein complexes may incorporate a fluorescence moiety which is quenched on ion binding, or protein complexes which incorporate a fluorescence moiety and quencher, the latter which is removed on binding of the ion causing a release of light.

Different ions may be detected using different complexes. Magnesium is detected with fluorescent dyes such as Mag-Fura-2 and Mag-Fura-5. They could be used to measure magnesium in situ (excitation 340-380 nm, emission 500-510 nm). Preferably the dyes are not toxic.

A number of dyes are calcium sensitive but may be too toxic to use in mouth. Fura-2, Calcium Green-1, Fluo-3, Indo-1 and cSNARF-1 are all fluorescent dyes, which bind to free intracellular calcium. Indo-1 and cSNARF-1 are dual emission dyes. Fluorescent calcium binding dyes used to detect and measure free calcium may be useful as an alternative to luminescent photoproteins. Furthermore, these dyes may be used in a novel method for simultaneous measurement of Calcium and Strontium in saliva if used in conjunction with Halistaurin. Fura-2, Calcium Green-1, Indo-1 and their actetomethyl ester derivatives have been used in mice (in vivo) to monitor neuronal activity. Rhod-2 is also a calcium sensitive dye although it is less sensitive than Fluo-3. The longer excitations and emissions wavelengths of Rhod-2 (~556/576 nm) make the indicator useful for experiments in cells and tissues that have high levels of autofluorescence and for experiments where another fluorescent dye of shorter wavelengths is used at the same time. As enamel is known to fluoresce, such long emission wavelength would be a significant advantage.

Detection of fluoride may be achieved with fluorescent dyes. High levels of fluoride are generally found in caries lesions, believed to be due to high uptake of the ion at sites of demineralisation. There has been and continues to be a great deal of research into fluoride sensitive fluorescent systems for both industrial and medical applications. One such complex is Zr(IV)-EDTA-oxine which exhibits a decrease in fluorescence upon fluoride binding. Fluoride sensors displaying an increase in fluorescence in the presence of fluoride have also been reported; these include boronic acid compounds and thioureido naphthalene derivatives. The boronic acid compounds are currently relatively insensitive (detection level 50-70 mM), however it is believed that with the appropriate modifications fluoride selectivity could be fine tuned to any desired concentration range. The novel thioureido naphthalene derivatives exhibit a 40-fold increase in fluorescence in presence of fluoride, and have a very high selectivity for fluoride over other halogens. Alternatively, (Tae-Hyun Kim and Timothy M. Swager (2003, Chem. Int. Ed. Angewandte 42, 4803-4806)

describes a system whereby the cleavage of a Si—O bond by fluoride leads to the formation of a highly fluorescent coumarin molecule.

Detection of potassium may be with a fluorescent dye such as SBFI, which is both potassium and sodium sensitive (excitation 340-380 nm, emission 510 nm). Potassium is linked to dental hypersensitivity and possibly caries. Alternatively, a photoprotein, derived from okinawan squid (*Symplectoteuthis oualaniensis*) is sensitive to potassium and may be used (US2004191884).

Where the composition includes a protein or protein complex, it may produce an optical signal on binding with free ions. Such a protein or protein complex may be modified, for example by altering the DNA sequence of the gene, by acetylation, ethoxycarbonylation, fluorescamine-modification or fluorescein labelling or by creation of chimeric proteins such as a GFP-aequorin (US2003175807) to enhance the signal, prolong the duration of signal or alter its emission spectra. Proteins and protein complexes with similar function, such as those undergoing a conformation change on binding to ion or organic material that leads to an optical signal may also be used.

Examples of such protein or protein complexes are photoproteins. Photoproteins are stable enzyme-substrate complexes consisting of polypeptide chain(s) and an oxygen-preactivated substrate, such as 2-hydroperoxycoelenterazine, which is tightly but noncovalently bound with the protein. Bioluminescence may be triggered by, for example, $Ca^{2+}$ and results from decarboxylation of the substrate bound with the protein. Another photoprotein which may be of use according to the invention is halistaurin. Halistaurin can be used to detect strontium, which is thought to replace a small fraction of the calcium in the hydroxyapatite crystal during mineralization. Deficiency in strontium is linked to dental caries ("*Strontium and dental caries*". Nutr Rev 1983; 41:342-344). Detection of strontium may be with a photoprotein such as halistaurin. Wide ranges of values of strontium in teeth (e.g. 66-564 ppm) have been reported from different areas in US.

Another example of a photoprotein is aequorin, which naturally occurs in the bioluminescent jellyfish, *Aequorea victoria* or can be expressed recombinantly. Aequorin is a protein capable of storing a large amount of energy, which is released in the presence of calcium. Apoaequorin interacts with its substrate coelenterazine to form a relatively stable complex, which is activated by calcium. The binding of two calcium ions to aequorin causes conformational changes of the protein, resulting in the opening of the protein and decomposition of coelenterazine peroxide to coelenteramide and $CO_2$, accompanied by emission of an optical signal or light. Further description of aequorin may be found in Shimomura et al (1978) *Proc. Natl Acad. Sci. U.S.A.* 75, 2611-2615; Head et al (2000) *Nature* 405, 372-376; and Shimomura (2005) *Journal of Microscopy* 217, 3-15.

Other examples of photoproteins include obelin, clytin, mitrocomin, halistaurin, phialidin, mnemiopsin, symplectin, gr-bolinopsin and berovin. These photoproteins show high sequence homology and contain three "EF-hand" calcium-binding sites. Further description of these photoproteins may be found in Prasher et al, Biochem. Biophys. Res. Commun. 126 (1985); Inouye et al, Proc. Natl. Acad. Sci. USA 82 (1985), pp. 3154-3158; Prasher et al, Biochemistry 26 (1987), pp. 1326-1332; Inouye et al, FEBS Lett. 315 (1993), pp. 343-346; T. F. Fagan et al, FEBS Lett. 333 (1993), pp. 301-305; Illarionov et al, Dokl. Akad. Nauk 326 (1992), pp. 911-913; Marionov et al, Gene 153 (1995), pp. 273-274; Shimomura et al (1985), Biochem J. June 15; 228(3):745-9; Ward et al (1974) Biochemistry. March 26; 13(7):1500-10. Further description of the mode of action of these proteins may be found in Markova et al, *Biochemistry* 41 (2002), pp. 2227-2236; Charbonneau et al, *Biochemistry* 24 (1985), pp. 6762-6771; Tsuji et al, *Photochem. Photobiol.* 62 (1995), pp. 657-661.

The composition may comprise a synthetic ion chelator such as an EDTA-reporter complex or a macrocycle such as a crown ether reporter complex. There are many examples of these, which bind to ions and complexes with reporters have been made. For example, joining of a fluorophore and selective receptors using photoinduced electron transfer for calcium using BAPTA as described in John F. Callan, A. Prasanna de Silvaa and Nathan D. McClenaghanv (2004) Chem. Commun. 2048-2049. Also U.S. Pat. No. 5,409,835 describes fluorescent calcium-binding heterocyclic probe compounds for determining calcium ion concentration in samples.

The composition may comprise a complex that fluoresces at a characteristic wavelength indicative of the presence of ions. Such fluorescent complexes respond to ions by altering the intensity or colour of light. These complexes may be proteins or protein complexes.

Preferred examples of fluorescent proteins include, cameleon proteins or indicators. Cameleons are a new class of indicators for calcium ion concentrations in living cells, which operate through a conformational change that results in "Förster Resonance Energy Transfer" (FRET or "Fluorescence Resonance Energy Transfer") in the presence of calcium ions. FIG. 1 shows a schematic representation of FRET in chameleon indicators. More specifically, FRET involves the non-radiative transfer of excitation energy from and excited donor fluorophore to an acceptor fluorophore in the ground state by means of intermolecular long range (10-100 Å) dipole-dipole interactions. Cameleon indicators consist of an artificial protein modified from green fluorescent protein (GFP). The cameleon molecular structure is modeled as a fusion product between two fluorescent proteins (having differing excitation and emission characteristics), calmodulin (CaM), and the calmodulin-binding domain of myosin light chain kinase (M13). Calmodulin is capable of binding with free calcium ions and the M13 chain can bind with calmodulin after it has bound the calcium ions. The genes of these four proteins are joined linearly, and the fusion genes are expressed in a variety of cells. When calmodulin binds free calcium, it changes in structure, bringing the two fluorescent proteins closer together and results in FRET. Thus, instead of the cyan fluorescent protein emitting blue light, this light is transferred to the yellow fluorescent protein, resulting in yellow fluorescence. Further description of cameleon indicators may be found in Miyawaki et al (1997) *Nature* 388 (6645):882; Miyawaki et al, Proceedings of the National Academy of Sciences (USA) 96: 2135-2140 (1999).

A further example of fluorescent protein is Pericam, which is a modified form of GFP. The $Ca^{2+}$-induced interaction between CaM and the binding peptide M13 of pericam leads to changes in the fluorescence characteristics of circularly permuted (cp)YFP as described in Nagai et al, PNAS 98 (6): 3197 (2001).

A further example of a fluorescent approach is the Camgaroo probe in which the binding of calcium interacts with calmodulin causing a protein conformational change and an increase in fluorescence from the yellow fluorescent protein and induces an increase in fluorescence (as reviewed in Rüdiger Rudolf, Marco Mongillo, Rosario Rizzuto & Tullio Pozzan *Nature Reviews Molecular Cell Biology* 4, 579-586).

A further example of a fluorescent approach are the chimeric fluorescent-photoproteins for example GFP-aequorin (such as US2003175807) wherein the fluorescent molecule is covalently linked with a photoprotein and there is a transfer of the energy by Chemiluminescence Resonance Energy Transfer (CRET).

These examples serve to illustrate the use of protein-reporter complexes in ion detection. The proteins involved may be any number that bind, or change conformation on binding a particular ion. For calcium these could be casein, calsequestrin, calexcitin, calcium binding cysteine protease, calmodulin and other EF hand proteins. The reporters may be dyes or fluorescent or luminescent proteins.

The composition may comprise a complex incorporating a molecular probe such as Scorpion probe, Taqman probe, Holliday junction or linear probe. Fluorescence or luminescence may occur on ion binding to the probe. Preferred examples of molecular probes are Holliday junctions. These are mobile junctions formed between four strands of DNA. They are usually used for detection of specific DNA sequences, however, metal ions are known to play an important role in determining the conformation of the junction by binding to particular sites (Thorpe J. H., Gale B. C., Teixeria S. C. and Cardin C. J. (2003) *J Mol Biol.* 2003 Mar. 14; 327(1):97-109). These junctions could therefore be used to detect the presence of ions such as sodium, calcium and strontium.

A number of methods may be used together. For example, chelators may be used to sequester one ion, leaving another to bind to a photoprotein. Thus the photoprotein halistaurin binds both calcium and strontium. Strontium may be a good measure of disease and the calcium, which would otherwise mask the amount of strontium present, could be sequestered before the photoprotein is added to the tooth, leaving the photoprotein to respond only to the strontium. Calcium sequestering agents could be protein based (calmodulin, calcyclin) or chemical based (BAPTA, EGTA). BAPTA (1,2-bis(o-aminophenoxy)ethane-N,N,N',N'-tetraacetic acid) is a calcium-specific chelator, and BAPTA based compounds are among the most popular for measuring free intracellular $Ca^{2+}$.

Photoproteins and fluorescent proteins may be used together using Bioluminescence Resonance Energy Transfer (BRET) in which the optical signal produced from a photoprotein is transferred to a fluorescent protein in close proximity, and fluorescence from the fluorescent protein is then measured. In this manner, the colour of the signal may be altered or the duration of the signal increased to improve imaging. One of the problems with imaging fluorescent dyes on teeth is that there are often situations where it is not practical to use a high intensity light source due to the intrinsic high auto-fluorescence of teeth. One possible benefit of using BRET is that it can be used for the excitation of a fluorescent probe that is co-localised in a specific area where calcium is present.

The composition may be used for in-mouth analyses, for example to detect the presence of active caries; and out-of-mouth analyses, such as in a laboratory for the study of artificially induced caries, development of new tooth-friendly foods and formulations and study of the erosivity of foodstuffs. Out of mouth analyses using the composition may also be carried out using a tooth model, such as hydroxyapatite models or enamel sections.

The composition may be used for example by dentists and dental hygienists, for early detection of active demineralisation, determination of the best treatment, for monitoring a problem or treatment over time, and identifying individuals who may be susceptible to certain dental problems (e.g. erosion or hypersensitivity); by laboratory researchers for the development of novel products (e.g. toothpastes, drinks); or for the home care market for detection and assessment of active dental disease (e.g. in the form of a mouthwash or disclosing tablets).

No single-step method for the detection of active caries is currently available. Active caries tend to produce free ions due to continued demineralisation; inactive caries will produce few, if any, free ions, due to the absence of demineralisation. Demineralisation may be detected by measuring the optical signal output following application of ion-sensitive reporters, this may be compared to non-active caries where there is little or no demineralisation.

Ion-sensitive reporters can therefore provide a one-time measure of the active nature of caries, and eliminate the need for multiple visits to the dentist. Ion-sensitive reporters may also be used to determine the susceptibility of an individual to dental disease, for example, dental erosion. In this case, a mildly eroding solution e.g. weak acid could be added to teeth and the response of the teeth as measured by a signal emitted by the detection composition would indicate the extent of demineralisation and likelihood of encountering problems with erosion in the future.

The method for the detection of active tooth demineralisation may optionally include the steps of removing saliva from the tooth surface, and where appropriate removing plaque (if present), then exposing the tooth surface under investigation to a composition as described above and detecting the resulting optical signal.

The method may further comprise the step of exposing the tooth to a sensitising solution, such as a sugary or acidic solution, prior to exposure with the protein composition. The sensitising solutions mimic the effects of demineralisation in order to detect hypersensitivity and erosion and may be used to assess the extent of a particular problem. For example, an acid solution may be used to identify areas of dentine (e.g. from tooth erosion) or root exposure (e.g. from receding gums). This is because particular parts of the tooth will respond more strongly to acid solutions than other parts and so can be identified. For example, due to the lower extent of mineralization within dentine and cementum, compared to enamel, addition of a sensitising solution will cause the release of more calcium from the dentine and cementum than the enamel. Upon application of the ion-sensitive reporter, the regions of dentine (corresponding to regions of dentine erosion or hypersensitivity) will be brighter, i.e. with a stronger optical signal, than regions of enamel so indicating the extent of the problem. This may improve the accuracy of the results.

Sensitising solutions may also be used to assess the susceptibility of an individual for a particular condition. Those individuals more susceptible to tooth erosion will show more demineralisation and so a greater response. Enamel structure and make up is less important in assessing susceptibility to dental erosion than saliva. Salivary composition, volume, composition and flow pay an important role in determining an individual's erosion susceptibility. The technology of the invention may be able to determine the resistance of the tooth enamel to acid challenge including the protection afforded by the individual's saliva (in particular the salivary pellicle). Such a quantitative test may be beneficial to dentists and dental hygienists to determine patient susceptibility and to monitor treatment and toothpaste developers and food scientists wanting to understand what effect changes to formulations have on level of demineralisation. Additionally this test will be useful in the promotion of new erosion prevention coatings. Therefore, an alternative version of the test for demineralisation due to erosion may involve waiting for a period of time, for example less than 1, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 seconds after exposure to the eroding solution so that the saliva can build up in the mouth, and then testing the extent of demineralisation with the detection composition. The period of time could be extended as necessary up to 1, 2 or 5 minutes for the saliva to build up again.

The resulting optical signal may be detected using a spectrophotometer, charge coupled device (CCD), complementary metal-oxide semiconductor (CMOS), digital camera, intensified camera, photographic film, fibre-optic device, photometric detector, photomultiplier micro-electromechanical system (MEMS) or visually by eye. For laboratory testing, for example in the development of tooth-friendly drinks, the process may use a camera, luminometer or fluorometer for automation and high throughput of samples.

Software may be used to analyse the intensity of the light, the location of the light and the duration of the light produced. It can be used to enhance the signal and provide a "superimposed" overlay on an image of the teeth to enable dentists to accurately target the sites and to aid in monitoring changes in time or after treatment.

Thus, the present invention also allows the assessment of the potential for further erosion, as well as dentine hypersensitivity (through demineralisation causing further opening of exposed dentinal tubules), by determining the amount of free calcium. Thus, the method allows the identification of patients more susceptible to tooth erosion, as well as hypersensitive teeth. This would allow preventive measures to be adopted by those individuals who are prone to erosion and may also allow laboratory-based tests to investigate new toothpastes for hypersensitivity, or to analyse food or drink products for their tooth-eroding properties.

The following experiments were carried out using an image based luminescence technique and the ion-sensitive protein aequorin. All work was carried out using extracted human teeth. In the mouth, a variety of methods of application could be used. For example, there may be a carrier device for the disclosing composition. This may be a mouthpiece such as a dental tray. An advantage of using a carrier device is that it keeps saliva away from the tooth and the disclosing composition. The tray may be non-customised i.e. only has approximate shape and size of person's mouth, or customised i.e. uses a person's teeth as a template to make the tray. The tray would act as an interface between the disclosing composition and the detector. Preferably the carrier device is optically clear. The disclosing composition may be added to carrier device before being placed in a patient's mouth or injected in to carrier device when in the mouth. Alternatively a strip of the disclosing composition may be used. This would be akin to tooth bleaching strips known in the prior art, which are applied to the area of interest. Conventional bleaching strips comprise a flexible plastic strip coated with a dental bleaching gel of moderate viscosity and relatively low stickiness on the side of the strip facing the user's teeth. Alternatively the disclosing composition could be sprayed on teeth or applied in a mouthwash.

An aequorin solution was prepared as follows. Recombinant aequorin was expressed in E. coli using the gene sequence originally from Aeguorea Victoria, complexed with the substrate coelenterazine, and lyophilized. The dry stock preparation contained approximately 1% aequorin w/w in mannitol (Prolume®). To make a working aequorin solution for application to teeth, the dry stock aequorin preparation was dissolved at a concentration of 1 mg/ml w/v in calcium-free purified water. Alternatively 1 mg/ml w/v aequorin was prepared in 1% Akucell 3625 gel with 1 mM EDTA. When calcium ions are added to this aequorin solution or gel, a flash of blue light is emitted.

Samples were placed in a dark box on a height-adjustable stage and images were recorded using a low light charge coupled device or CCD (Starlight Xpress HX-9® thermoelectrically cooled CCD camera fitted with a Tamron® macro lens). In most cases, hardware pixel binning of 2×2 was used to increase the sensitivity of detection and reduce exposure times. Images were saved as TIF files. Daylight images were captured with the dark-box door open allowing ambient light to illuminate the samples, and captured using $10/100^{th}$ second exposure and 2×2 binning. Dark images were taken with the dark box door closed, and using a 1 or 2 minute exposure time, with 2×2 pixel binning.

Grayscale (256 levels) images were opened in Image J and (if necessary) the contrast adjusted to increase the clarity of the image, before being inserted to Microsoft Word® document. For images produced for the same experiments the same adjustments were made to each image. The resulting images can be used to map the luminescence, corresponding to the presence of calcium on the sample. The darkest regions (black) indicate regions of lowest light and the lighter regions (white) indicate regions of increasing light.

Experiment A: Demineralisation of Teeth Using Acid Gel

A standard method used in the industry to mimic generation of active caries in the laboratory is to create regions of demineralisation using acid solutions or gels (for example reference Amaechi et al.: Arch Oral Biol 1998; 43: 619-628). We have carried out similar experiments in order to determine whether our disclosing material can be used to identify regions of demineralisation.

Figure 2:
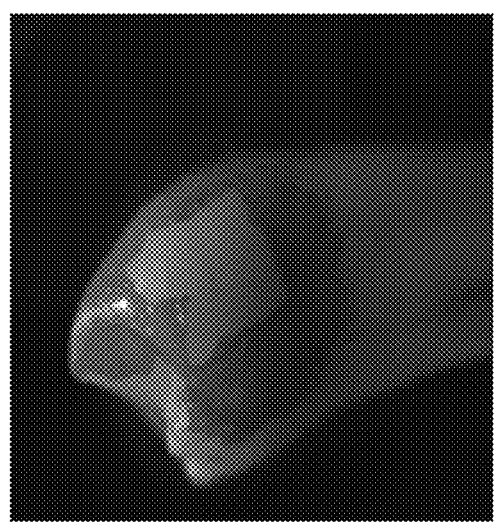
FIG. 2 shows extracted premolar teeth with masked 'windows' marked on the surface thereon.

Carboxymethylcellulose (3% w/v Akucell 1985) gel was prepared at pH 4.7 or pH 6.4 (using 0.1M lactic acid, neutralised with 5M potassium hydroxide). This pH range was chosen since enamel dissolves at a critical pH of approximately 5.4. 'Windows' of approximately 4×4 mm were created on the smooth surfaces of extracted premolar teeth using nail varnish, FIG. 2. Windows were of similar size (since the size is known to affect the extent of mineral loss). Gel (either pH 4.7 or 6.4) was applied to the window and the tooth incubated in a hydrated environment and 37° C. for 5, 10, 14 or 21 days. 5 replicate teeth were used at each timepoint and pH. In addition, 15 teeth were incubated for 14 days in either gel of pH 4.7, assessed, then incubated with gel of either pH 4.7 or pH 6.4 for a further 5 days before being reassessed. This allows determination of whether demineralization can be halted by neutralizing the gel.

After incubation, the gel was gently wiped from the tooth surface with tissue and the surface rinsed with deionised water. The tooth was imaged with a Sony HX9 camera using 2×2 binning and image capture time of 10 ms in the light. 0.2 cm³ of 1 mg/cm³ aequorin in 1% Akucell 3625 gel (disclosing gel) prepared with 1 mM EDTA was transferred to tooth with an automatic pipettor. A 1 minute image with 2×2 binning was taken immediately in the dark.

Figure 3:
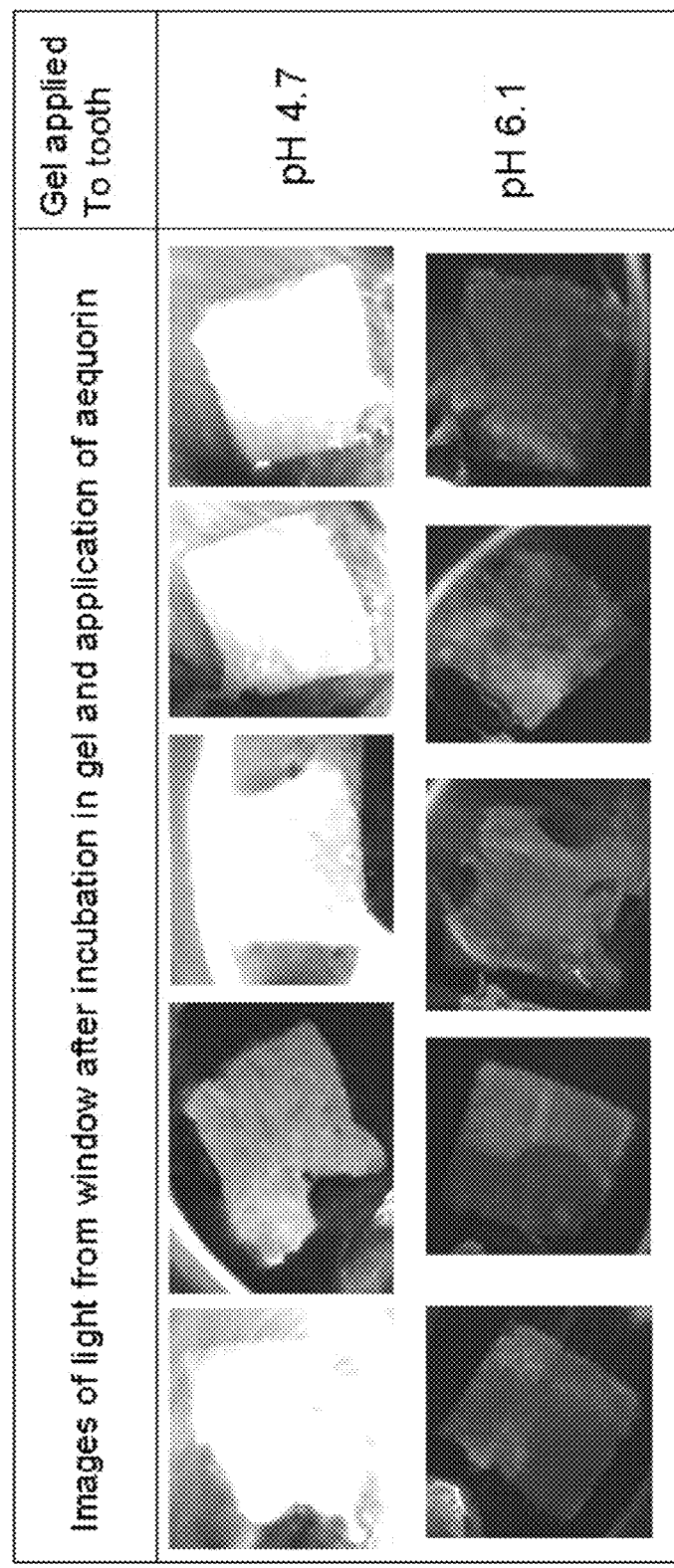
FIG. 3 shows images of extracted teeth following application of acid gel and disclosing gel.
Figure 4:
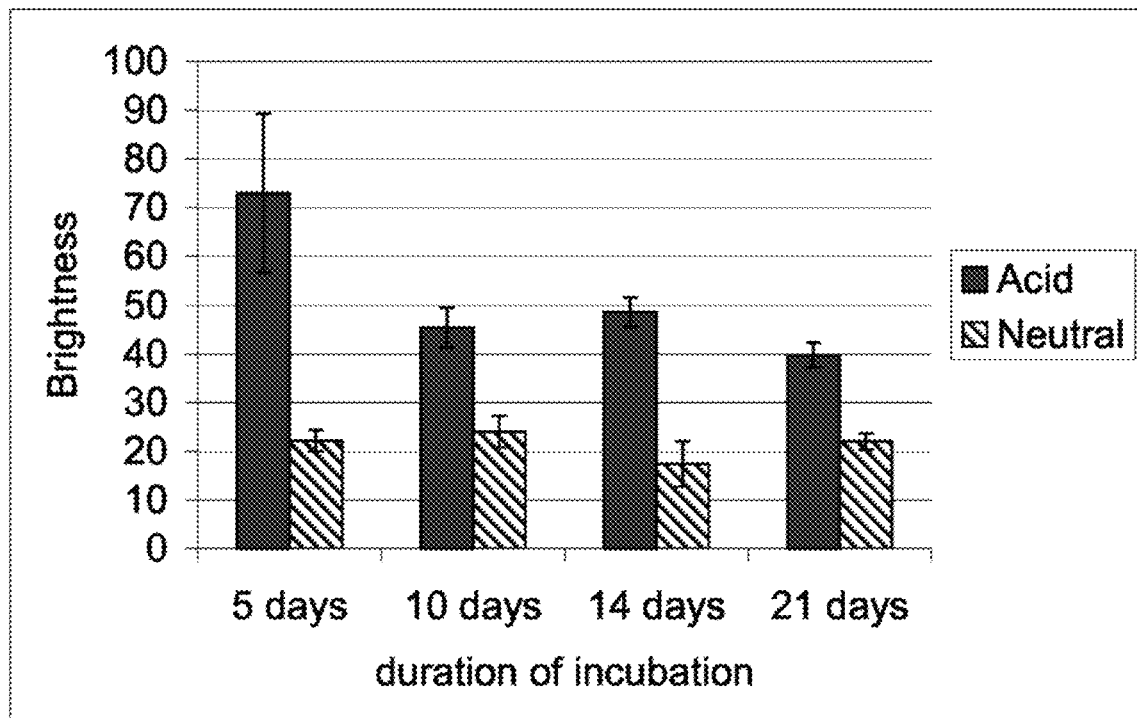

Example images are shown in FIG. 3. The contrast of images was altered to improve presentation and exactly the same adjustments were applied to all images. Image J was used to determine the brightness of the area within the windows, FIGS. 4 and 5.

The results clearly shows that those teeth incubated with gel of pH 4.7 showed higher levels of light i.e. free calcium release and demineralization than those incubated with gel of pH 6.4. Further, light output was reduced when teeth were incubated first in acid gel and then transferred to neutral gel, as compared to teeth transferred from acid gel to acid gel.

These results provide robust evidence that calcium sensitive photoproteins such as aequorin can detect areas of demineralization. Significantly, the demineralization could be detected after only 5 days. This is earlier than other techniques described in published literature, providing evidence that this method will provide data for very early demineralization.

Experiment B: Use of Alternative Disclosing Materials

There are a number of materials that can be used to identify regions of demineralization by determining ion release. Example A used the photoprotein aequorin. Other materials may also be used.

FIG. 6 shows how obelin (a calcium sensitive photoprotein) may also be used. An extracted tooth was incubated in 1% citric acid for 2 minutes. Acid is known to cause demineralisation of enamel. The tooth was removed, rinsed in deionised water then assayed. The tooth was imaged with a Sony HX9 camera using 2×2 binning and image capture time of 10 ms in the light. 0.2 cm$^3$ of either 1 mg/cm$^3$ aequorin or 50 ug/ml obelin in 1% Akucell 3625 gel (disclosing gel) prepared with 1 mM EDTA was transferred to tooth with automatic pipettor. A 1 minute image with 2×2 binning was taken immediately in the dark. To improve presentation, image contrast was adjusted using ImageJ; the same adjustment was made to both images. FIG. 6A shows light generated from aequorin gel and 6B from obelin gel. Results indicate how a number of different reporters may be used to indicate the presence of free ions and demineralisation.

Experiment C. Exposure of Roots

An extracted tooth was immersed in aequorin to test whether all areas of the tooth responded in the same manner to aequorin solution. The tooth was lightly brushed with calcium-free purified water and placed in a 3 cm diameter Petri dish in a dark box. A daylight image was acquired using the CCD camera.

5 ml of 1 mg/ml aequorin solution was pipetted directly onto the surface of the tooth. An image was immediately acquired, using a 2 minute exposure, with 2×2 binning. The root of the same tooth was then 'masked' with liquid latex (CopyDex®) and aequorin solution added again and the image taken as before. Results are shown in FIGS. 7A and 7B.

Figure 7A:
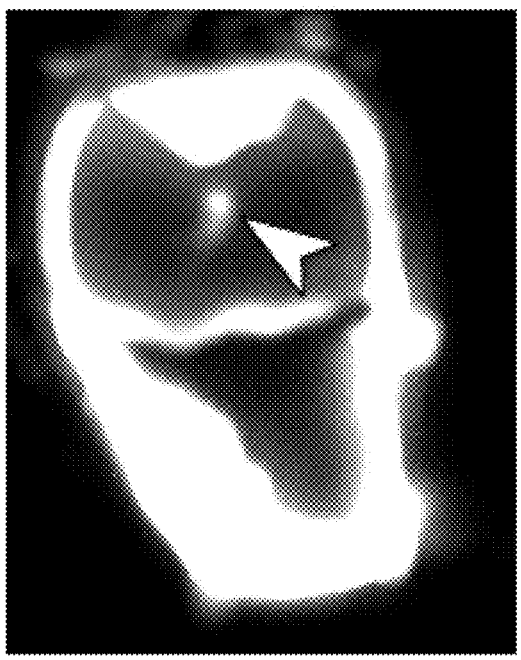
FIGS. 7A to 7B show the results of experiments carried out on the root of a tooth with a caries.
Figure 7B:

FIGS. 7A and 7B are images of a tooth after exposure to aequorin, and a root of tooth masked with copydex® before exposure to aequorin, respectively. In FIG. 7A, the lighter areas (greatest luminescence) correspond to the root and in FIG. 7B, there is an absence of light from the root area that has been masked. The light output is slightly different due to re-orientation of the tooth following masking. Arrow indicates the presence of caries in the crown of the tooth as evident as a white spot and confirmed by a dental clinician.

Results indicate that the root of the tooth reacts more strongly to the aequorin than does the crown, indicating a much higher amount of free calcium in the root. This is believed to be because of the lower mineralization of the root tissues (dentine and cementum) than enamel of the crown. A calcium-sensitive assay, such as the method described herein, using aequorin, may be used to identify exposed root tissue, e.g. as part of an investigation of hypersensitivity mechanisms. Alternatively, roots may be masked, e.g. with Copydex®, before addition of the aequorin allowing investigation of the crown without interference from the root.

Experiment D: Exposure of Dentine

Disclosing gels or solutions that identify demineralization due to ion release may also be used to detect and assess the extent and localisation of demineralisation that results from erosion (and indirectly hypersensitivity).

When the crowns of teeth become chipped—i.e. lose some of the enamel, the dentine of the tooth can be exposed. Similarly when teeth are eroded, e.g. by acid, dentine may be exposed. In this experiment a chipped tooth was used to investigate whether exposed dentine can be identified using a ion-sensitive reporter assay. An extracted tooth was lightly brushed with calcium-free purified water. A portion of enamel chipped off in the process, exposing the underlying dentine. The root of the tooth was 'masked' with liquid latex (CopyDex®). The tooth was placed in a 3 cm Petri dish in a dark box. A daylight image was acquired. 4 ml of 1 mg/ml aequorin solution was pipetted directly onto the surface of the tooth. An image was immediately acquired in complete darkness, using a 2 minute exposure, with 2×2 pixel binning. Results are shown in FIGS. 8a and 8b.

Figure 8A:
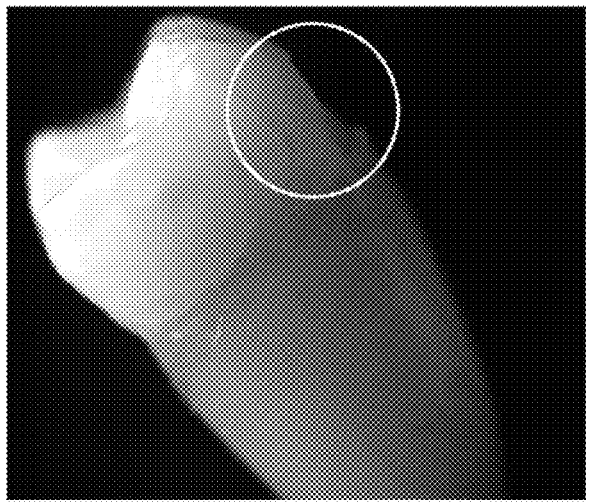
FIGS. 8A and 8B show the results of experiments carried out on the dentine on a tooth.
Figure 8B:
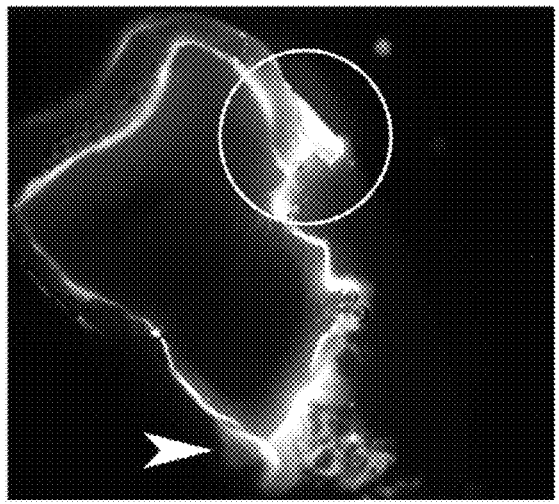

FIG. 8A is a daylight image of a tooth and FIG. 8B is an image of a tooth after exposure to aequorin. Circled area shows region of chip. Arrow indicates region of root not fully covered by CopyDex®.

Results indicate that much light was produced from aequorin in contact with the freshly chipped area of the tooth. This indicates that exposed dentine reacts with aequorin to produce light. An ion-sensitive reporter assay e.g. one using aequorin, could therefore be used to identify regions where dentine is exposed, for example after tooth erosion.

Experiment E: Cavity Identification

An extracted tooth was identified to have a cavity by a trained dental clinician. The root of the tooth was masked using CopyDex®. The tooth was lightly brushed with calcium-free purified water and placed in a 3 cm Petri dish in a dark box. A daylight image was acquired using a CCD camera.

5 ml of 1 mg/ml Aequorin solution was pipetted directly onto the surface of the tooth. An image was immediately acquired in complete darkness, using a 2 minute exposure, with 2×2 pixel binning. Results are shown in FIGS. 9A to 9B and 10A to 10B.

Figure 9A:
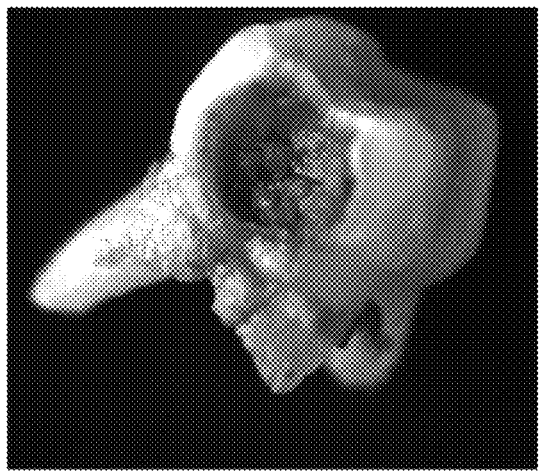
FIGS. 9A to 9B show the results of experiments carried out in relation to cavity identification.
Figure 9B:
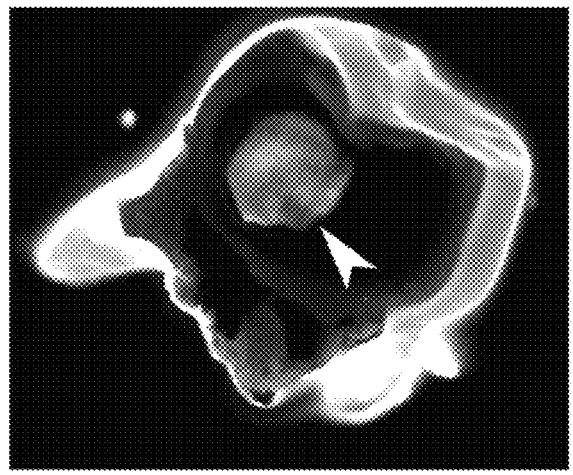

FIGS. 9A to 9B are (a) an image of a deciduous (or 'milk') tooth in the light, and (b) a monochromatic image. Following processing of the image regions of lower light appear in black, with grey and white indicating regions of increasing light. The arrow indicates the cavity identified by dental clinician.

Figure 10A:
FIGS. 10A to 10B show the results of further experiments carried out in relation to cavity identification.
Figure 10B:
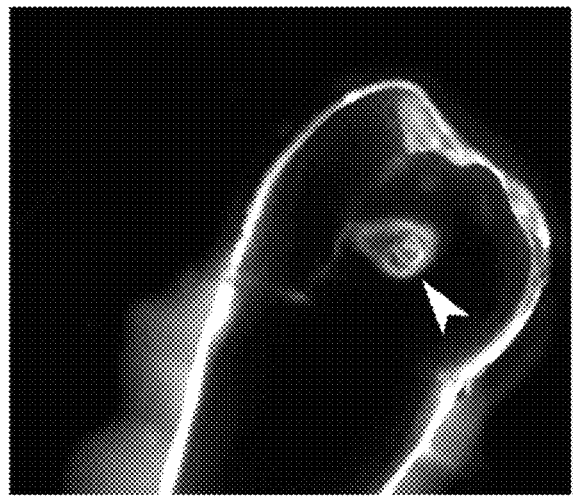

FIGS. 10A to 10B are an image of a permanent tooth in the light, and a monochromatic image respectively. Following processing of the image regions of lower light appear in black, with grey and white indicating regions of increasing light. The arrow indicates the cavity identified by dental clinician.

The composition according to the present invention responds to free ions by emitting light and the intensity of the optical signal is a measure of the quantity of free ions present. The duration of the light emitted indicates the nature of the ions released, e.g. a longer glow may indicate a continual release of ions or that released from deeper tissues. Different parts of the tooth respond differently to the ion-sensitive protein because of the chemical nature of the free ions present, e.g. dentine responds more than enamel because of the amount of mineralization. This can be used to identify tooth active caries, active erosion, exposed dentine after gums have receded, etc.

The location of the optical signal will indicate the location of the problem, e.g. the active caries. The size of the surface area of light indicates the extent of the problem, e.g. the surface area of the active caries. The duration of the glow can indicate the degree of the problem, e.g. the extent of the effect of the acid-challenge (i.e. the individual susceptibility of a tooth/patient to caries or erosion) or the type of tissue affected. Active caries may be distinguished from inactive caries by the intensity, duration or colour of the optical signal produced. In active caries demineralisation is continuous so more calcium is present and more signal is produced. A totally inactive lesion will produce only 'background' signal levels. A partially active lesion will show areas of activity and inactivity, i.e. areas with and areas without signal.

Thus, areas of demineralisation may be detected using ion-sensitive complexes prior to clinically visible caries lesion formation so that treatment, e.g. fluoride application, can be applied to prevent further progress of the decay process.

Experiment F: Caries Identification I

Laboratory studies can be used to create artificial caries, using acid solutions. Preferably, teeth extracted from the mouth and with caries are used to test the approach. These will have naturally-generated caries and provide a better mimic of teeth in the mouth.

An extracted tooth was identified to have caries by a trained dental clinician, after identifying a 'white' region under a bright light. This indicates an area of demineralisation and is a traditional method of identifying caries.

The root of the tooth was masked using CopyDex®. The tooth was lightly brushed with calcium-free purified water and placed in a 3 cm Petri dish in a dark box. A daylight image was acquired using a CCD camera.

5 ml of 1 mg/ml Aequorin solution was pipetted directly onto the surface of the tooth. An image was immediately acquired in complete darkness, using a 2 minute exposure, with 2×2 pixel binning.

Figure 11A:
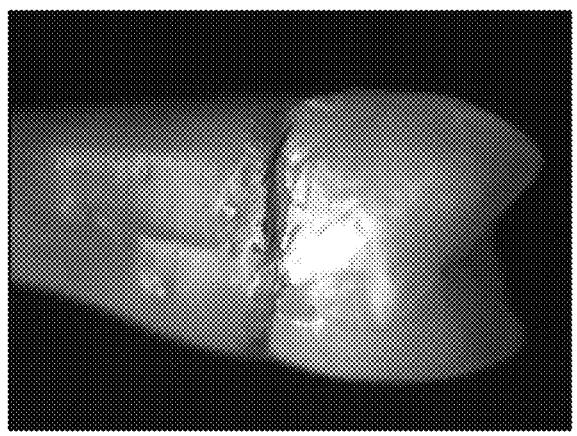
FIGS. 11A to 11B show the results of further experiments carried out in relation to caries identification.
Figure 11B:
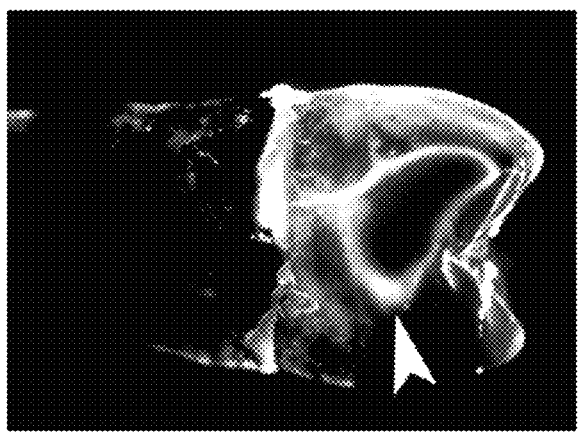

FIGS. 11A to 11B are a daylight image of a tooth in the light, and a greyscale image, respectively. Following processing of the image, regions of lower light appear in black, with grey and white indicating regions of increasing light. The arrow indicates caries identified by dental clinician using traditional methods.

As the images show the 'white' region identified by a trained dental clinician to be a caries lesion (active when the tooth was extracted) is identified as a brighter area in the aequorin assay. This indicates the aequorin assay can replace traditional 'by sight' methods.

Experiment G: Caries Identification, Assessment of Freshly Extracted Teeth

Teeth that had been extracted for orthodontic or other reasons were obtained immediately after extraction. No patient information was available, although some of the teeth were predicted by a dentist to have active caries due to the age (it was a clinic for minors) and condition of the teeth. Immediately after extraction, teeth were rinsed with deionised water to remove some of the adhering blood and biological material. The teeth were assayed immediately with disclosing gel.

Figure 12:
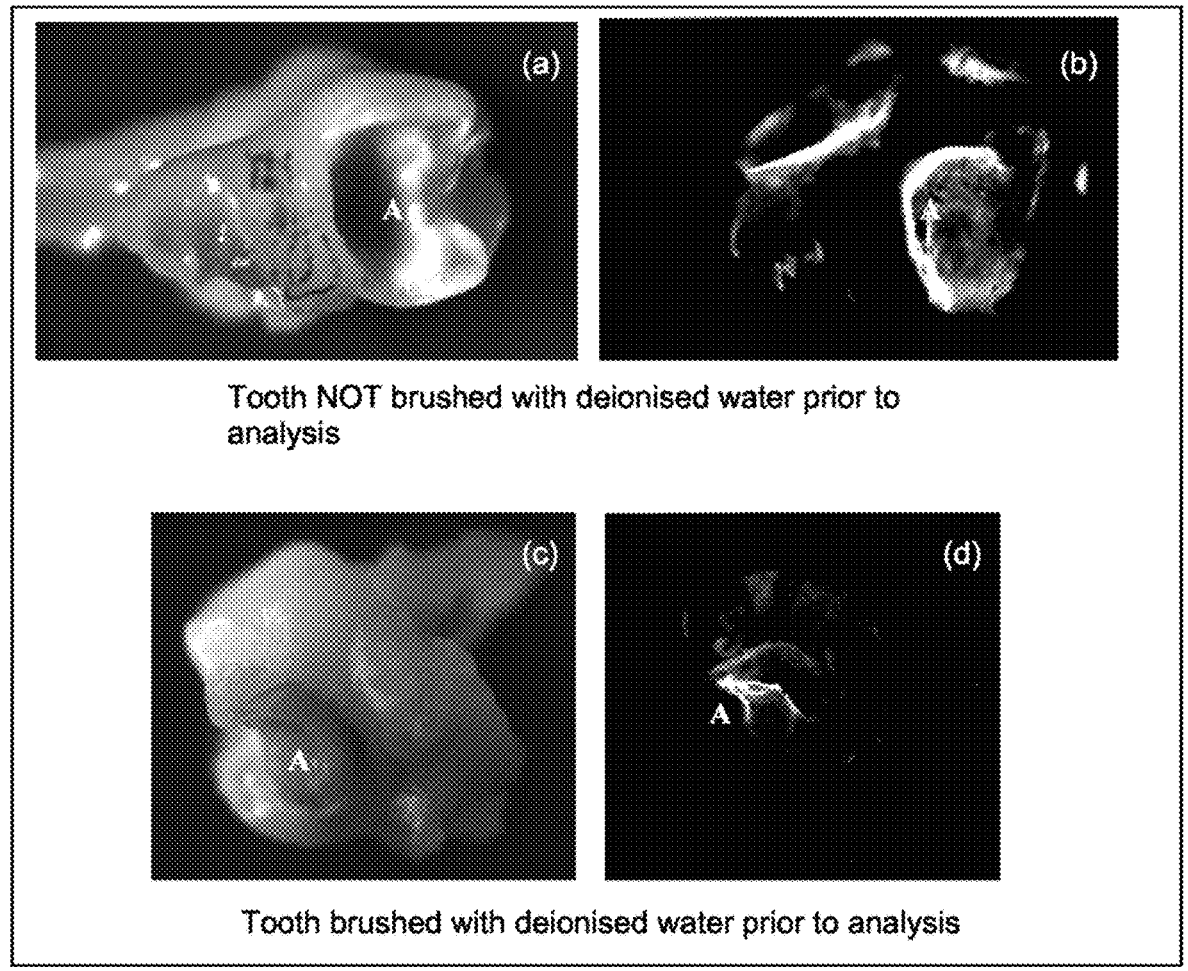
FIG. 12 shows images of deciduous molars with cavitated lesions (A).

The effect of brushing the extracted teeth in deionised water was determined by comparing light output from brushed and unbrushed teeth with cavitated lesions; FIG. 12. Limited effect was observed and so the remainder of teeth were brushed, as we consider this approach best mimics a patient's actions when visiting a dentist.

A dentist assessed the teeth for caries lesions and marked which side of the tooth to look at with pencil. This side was placed uppermost in a petridish and the tooth was imaged with a Sony HX9 camera using 2×2 binning and image capture time of 10 ms in the light. 0.2 $cm^3$ of 1 $mg/cm^3$ aequorin in 1% Akucell 3625 gel (disclosing gel) prepared with 1 mM EDTA was transferred to the tooth with automatic pipettor. A 1 minute image 2×2 binning was taken immediately in the dark.

Image J was used to alter the contrast of images, although differences are easily visible without image modification, this was carried out in order to better present the data. Regions of lower light appear in black, with grey and white indicating regions of increasing light. Results are shown in FIG. 13-16.

Teeth were then x-rayed in order to determine whether the regions of active demineralization identified in the photoprotein assay were visible by traditional methods. Although X-rays are used to monitor lesion progression caries that were detected with the disclosing gel were not visible by x-ray, FIG. 17. This indicates the usefulness in this approach for early identification of caries lesions.

Experiment H: Assessment of Interferences

Potential interferences by other products, for example toothpaste were investigated, because if light is produced in response to these then this assay could be problematic for in-mouth use.

Figure 18:
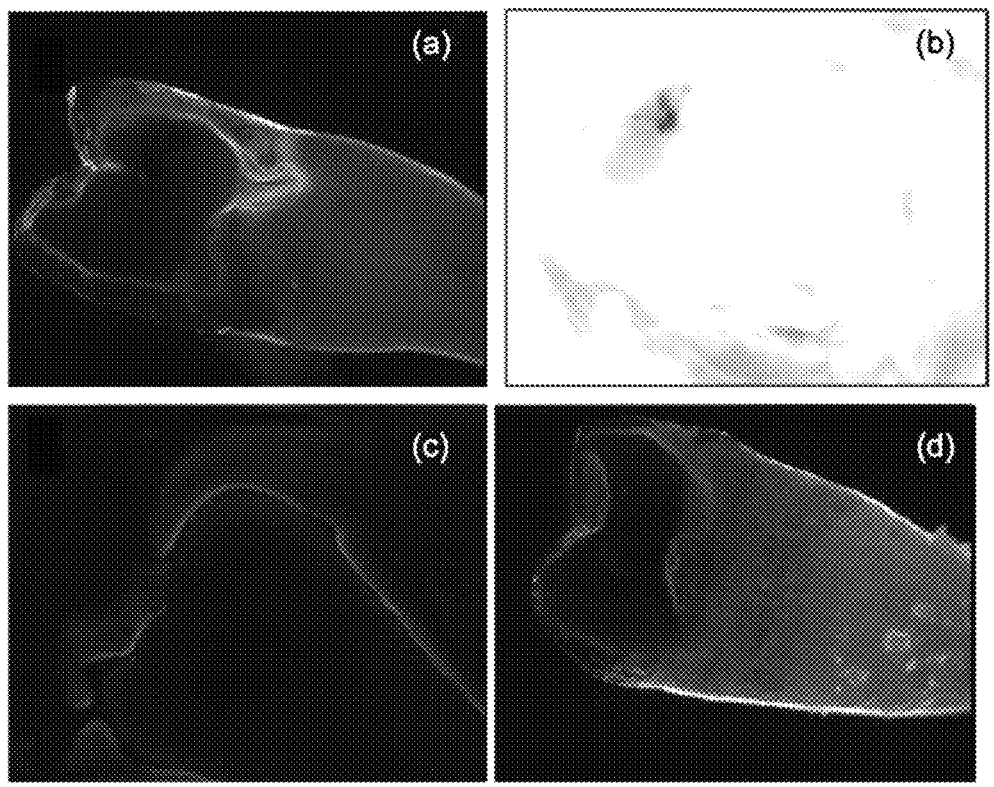
FIG. 18, panel (a), shows an image of a tooth that had been rinsed in deionised water and removed before being assessed.

Saliva: extracted teeth were rinsed in either deionised water or saliva (pooled from 8 individuals). Before addition of disclosing solution the teeth were imaged with a Sony HX9 camera using 2×2 binning and image capture time of 10 ms in the light. 5 $cm^3$ 1 mg/ml aequorin in deionised water was then added (disclosing solution) and imaged for 2 minutes, 2×2 binning in the dark. Teeth were either imaged in saliva, removed from saliva or removed and rinsed in deionised water FIG. 18. Results indicate that saliva contains significant quantities of calcium. However, providing the tooth is not in volumes of saliva it should not interfere with analysis. Even in the mouth the volume of saliva will be minimal and so saliva is not expected to be a problem for analysis.

Experiment H2: Calculus

Figure 19:
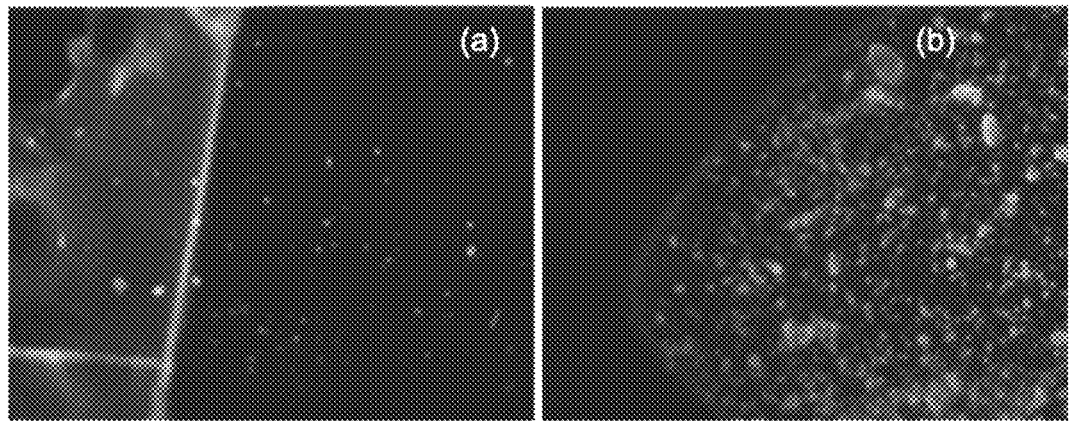
FIG. 19, panel (a), shows supra-gingival calculus imaged following addition of disclosing solution.

Calculus was obtained by scraping from teeth in the course of a dental treatment and was provided as flakes suspended in water. Both subgingival and supragingival were assessed. Samples were filtered before use with a Millipore membrane filter and holder, under vacuum and washed with deionised water. 5 cm³ 1 mg/ml aequorin in deionised water was added and the samples imaged for 1 minute, 2×2 binning. FIGS. 19A and 19B. Contrast was adjusted using ImageJ to improve presentation, the same adjustment was applied to both samples.

Figure 20:
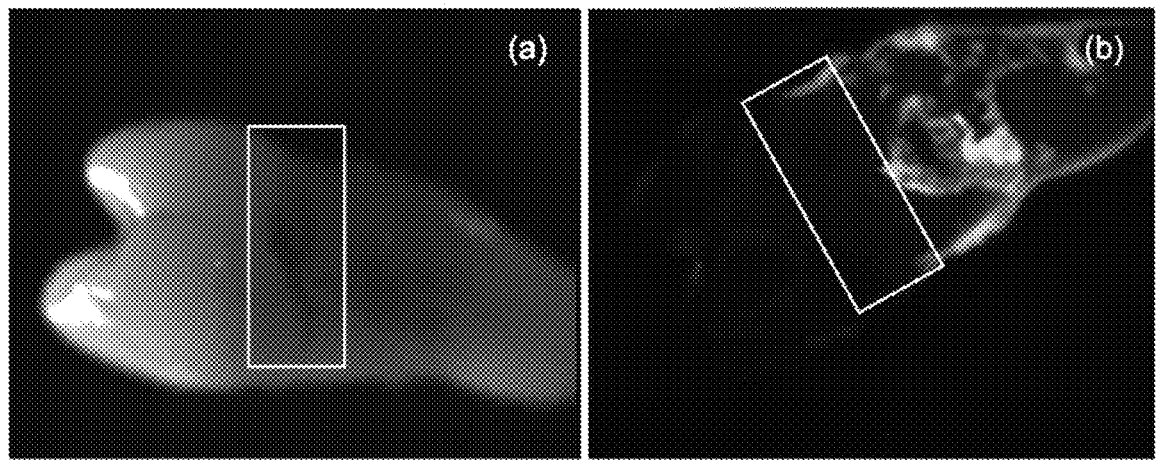
FIG. 20, panel (a), shows an image of the tooth in the light following application of disclosing gel; box indicates area of calculus.

The effect of in-situ calculus was also investigated. 5 cm³ 1 mg/cm³ aequorin 0 in deionised water was added and the samples imaged for 2 minute, 2×2 binning, FIG. 20

Experiment H3: Resin Filling

A tooth with a resin filling was assessed. The tooth was imaged with a Sony HX9 camera using 2×2 binning and image capture time of 10 ms in the light. 0.2 cm³ of 1 mg/cm³ aequorin in 1% Akucell 3625 gel (disclosing gel) prepared with 1 mM EDTA was transferred to tooth with an automatic pipettor. A 1 minute image 2×2 binning was taken immediately in the dark, FIG. 21.

Results indicate that small amounts of light were obtained but are likely to be too low to interfere with the assay. Indeed lower regions of light on a tooth may provide an indication of the presence of calculus.

Experiment H4: Toothpaste

Teeth were brushed with deionised water, or toothpaste and deionised water before being assessed with 2 cm³ of 1 mg/cm³ aequorin in deionised water. No extra light was visible from toothpaste-treated surfaces than controls indicating toothpaste should not interfere with the assay (data not shown).

Experiment I: Dental erosion and hypersensitivity

Carbonated soft drinks contain high levels of acid and are known to be a cause of tooth erosion and can exacerbate dentine hypersensitivity. A number of extracted teeth were incubated in these drinks and aequorin was used to assess their effects. This was undertaken with a view to developing an assay for dental erosion (and indirectly, hypersensitivity) or a method of identifying susceptible individuals.

Extracted teeth were lightly brushed with calcium-free purified water and toothbrush and placed in a 3 cm Petri dish in a dark box. A daylight image was acquired using a CCD camera. 5 ml of 1 mg/ml Aequorin solution was pipetted directly onto the surface of the tooth. An image was immediately acquired in complete darkness, using a 2 minute exposure, with 2×2 pixel binning.

The teeth were then rinsed with calcium-free purified water before being immersed in Cola, Irn Bru® or 1% citric acid for 10 minutes. Teeth were then rinsed with calcium-free purified water before 5 ml of aequorin solution was added, and the teeth imaged as before. The pH of the solutions was also assessed (with a Hydrus 300 pH meter®). All were acidic: Cola: pH 2.38; Irn Bru® pH 2.82; citric acid pH 2.17. Results are shown in FIGS. 22A to 22C, 23A to 23C and 24A to 24C.

Figure 22A:
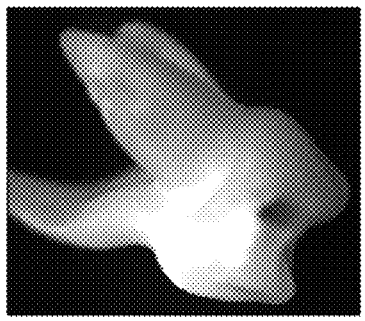
FIGS. 22A to 22C show the results of experiments carried out in relation to dental erosion and hypersensitivity.
Figure 22B:
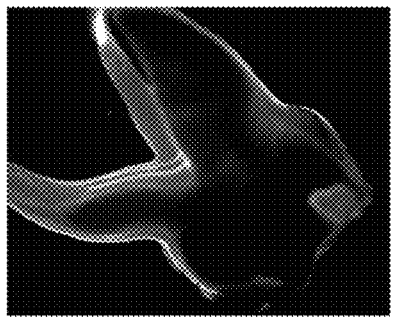
Figure 22C:
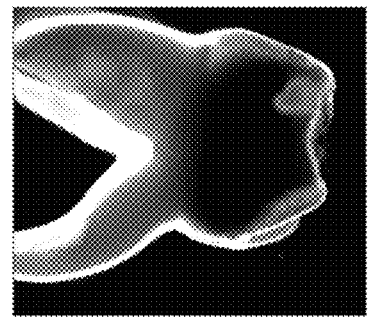

FIGS. 22A to 22C illustrate the effect of a 10 minute immersion in Cola. FIG. 22A is a daylight image of a tooth with no added aequorin; FIG. 22B is an image of a tooth in darkness after addition of aequorin, without any other treatment; and FIG. 22C is an image of a tooth in darkness after addition of aequorin and following a 10 minute incubation in Cola.

Figure 23A:
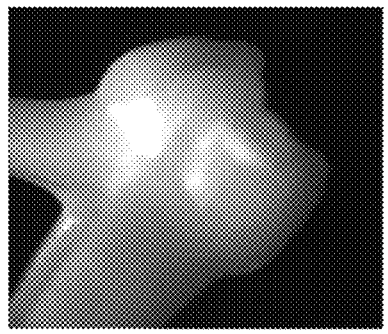
FIGS. 23A to 23C show the results of further experiments carried out in relation to dental erosion and hypersensitivity.
Figure 23B:
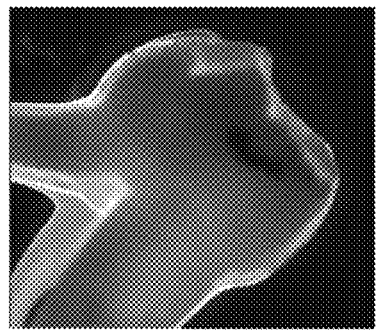
Figure 23C:
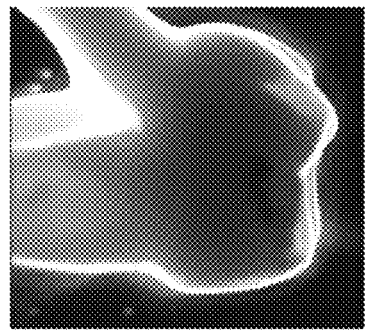

FIGS. 23A to 23C illustrate the effect of a 10 minute immersion in Irn Bru®. FIG. 23A is a daylight image of a tooth with no added aequorin; FIG. 23B is an image of a tooth in darkness after addition of aequorin, without any other treatment; and FIG. 23C is an image of a tooth in darkness after addition of aequorin and following a 10 minute incubation in Irn Bru®.

Figure 24A:
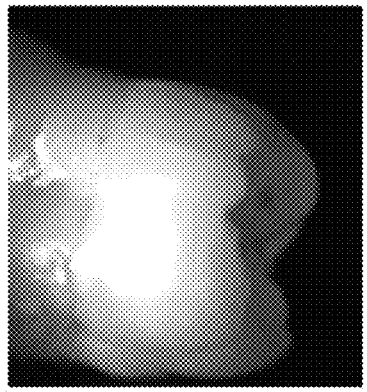
FIGS. 24A to 24C show the results of yet further experiments carried out in relation to dental erosion and hypersensitivity.
Figure 24B:
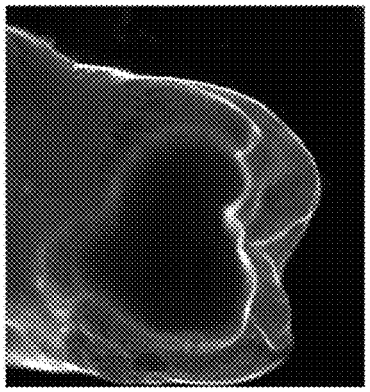
Figure 24C:
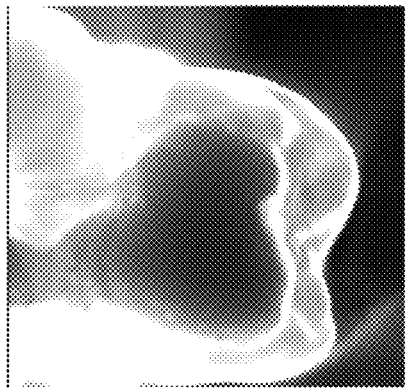

FIGS. 24A to 24C illustrate the effect of a 10 minute immersion in 1% citric acid. FIG. 24A is a daylight image with no added aequorin; FIG. 24B is an image of a tooth in darkness after addition of aequorin, without any other treatment; and FIG. 24C is an image of a tooth in darkness after addition of aequorin and following a 10 minute incubation in 1% citric acid.

Drinking carbonated drinks is known to cause tooth erosion. Results here show that after incubation with sugary carbonated drinks or acid solution, free calcium is released from teeth, which can be detected with aequorin. This was most pronounced on the root. Ion-sensitive proteins, such as aequorin, can therefore be used to indicate areas of calcium release and so indicate areas of demineralisation and in turn tooth damage such as erosion or increased likelihood of hypersensitivity.

In hypersensitive teeth, the dentine has more tubules open at the dentine surface (up to 8 times) and the tubule diameter is wider. This provides a greater available surface area for demineralisation, for example by acidic drinks, and will also lead to the release of more calcium following application of such products. This will be observed as a brighter region, as seen in FIGS. 22 to 24.

Experiment J: Acid Etched Teeth

Dental etching gel is used to roughen the tooth surface so that, for example, fissure sealants can be attached firmly. The etching gel is an acidic preparation that etches to a limited depth in a localised area.

Extracted teeth were lightly brushed with calcium-free purified water and toothbrush. A small (4×4 mm) label was applied to the tooth, and fixed in place by painting over the entire area of the label and surrounding surface of the tooth with nail varnish. This was allowed to dry then the label was peeled off, giving a 4×4 mm exposed area surrounded with varnish. This delimited the area to which the dental etching gel (Ultradent Products Inc) was applied. Etching gel was left for 5 minutes before being wiped off with a cotton swab, and rinsed off with damp cotton wool swabs.

5 ml of 1 mg/ml Aequorin solution was pipetted directly onto the surface of the tooth. An image was immediately acquired in complete darkness, using a 2 minute exposure, with 2×2 pixel binning. A second image was acquired immediately afterwards, using a 2 minute exposure. Results are shown in FIGS. 25a to 25c.

FIGS. 25A to 25C are a daylight image, with no added aequorin; a monochromatic image after addition of aequorin, with 2 minute exposure; and a monochromatic image after addition of aequorin, with sequential 2 minute exposure. The left arrow indicates nail varnish, the asterisk indicates the area the etching gel was applied to.

When aequorin was added to a tooth that had been etched with dental etching gel there was a bright flash of light, visible by eye. The second exposure resulted in less light emission than the first exposure. This indicates that the gel releases calcium from only a localised area, this is immediately available for reaction to aequorin, hence the flash, with little 'subsurface' calcium being released for light output to be prolonged.

This is unlike the effect observed with citric acid, where light output continued for some time. As shown in FIGS. 26A to 26D, the method as described in Experiment E was carried out with a second image, 5 min exposure, and acquired 15 minutes after the aequorin had been added. It appears that citric acid causes more extensive demineralisation.

FIGS. 26A to 26D illustrate the effect of a 10 minute immersion in 1% citric acid. FIG. 26A is a daylight image, with no added aequorin; FIG. 26B is an image of a tooth in darkness after addition of aequorin, without any additional treatment; FIG. 26C is an image of a tooth in darkness after addition of aequorin and following a 10 minute incubation in 1% citric acid, 2 minute exposure taken immediately after addition of aequorin; FIG. 26D is an image of a tooth in darkness after addition of aequorin and following a 10 minute incubation in 1% citric acid, 5 minute exposure taken 15 minutes after addition of aequorin.

Experiment K: Assessment of a Patient's Susceptibility to Erosion

Different people have a different susceptibility to erosion and hypersensitivity. This is known to be in part due to treatments such as fluorosis and positioning of the teeth although it is generally regarded that the most important factor influencing dental erosion prevention is saliva (flow rate, composition, buffering and remineralisation capacity).

The disclosing composition may be used to identify level of demineralisation caused by acid erosion of patients by first rinsing teeth in an acid solution. This will provide information on the susceptibility of the tooth itself for erosion. Further, by reassessing light output after addition of saliva to the teeth the role of an individual patient's saliva can be determined. The assays may be performed on extracted teeth or in the mouth.

To assess of demineralisation, the tooth was imaged with a Sony HX9 camera using 2×2 binning and image capture time of 10 ms in the light. 0.2 $cm^3$ of 1 $mg/cm^3$ aequorin in 1% Akucell 3625 gel (disclosing gel) prepared with 1 mM EDTA was transferred to tooth with automatic pipettor. A 1 min image with 2×2 binning was taken immediately in the dark. ImageJ was used to determine the brightness of the crown and root areas. A Glowell™ (blue G2, 96 well format) was included to ensure the uniformity of the light measuring equipment. Importantly, the aequorin is not pH sensitive and light output is similar across a large pH range. Extracted teeth were assessed as above (in triplicate). Teeth were incubated in 1% citric acid for 2 minutes, removed, rinsed in deionised water, assessed, then incubated in either deionised water or saliva for 30 s and then reassessed.

Figure 27A:
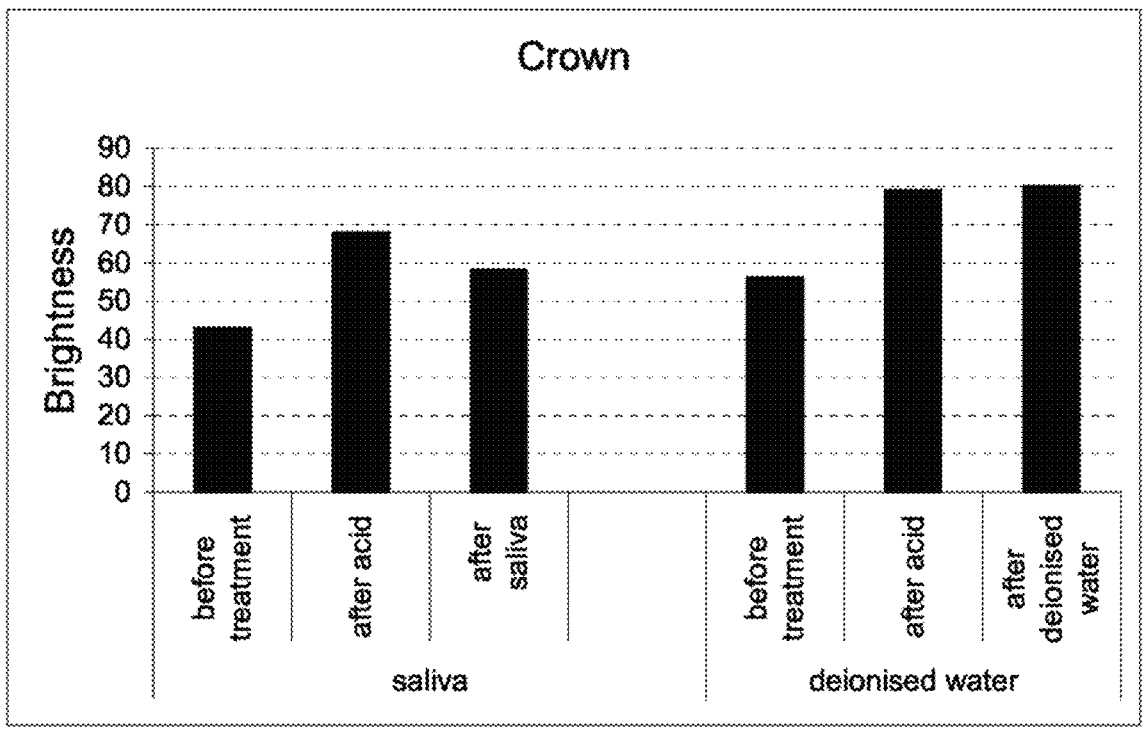
FIGS. 27A and 27B are graphs showing the protective effect of saliva on the acid-treated enamel compared to deionised water.
Figure 27B:
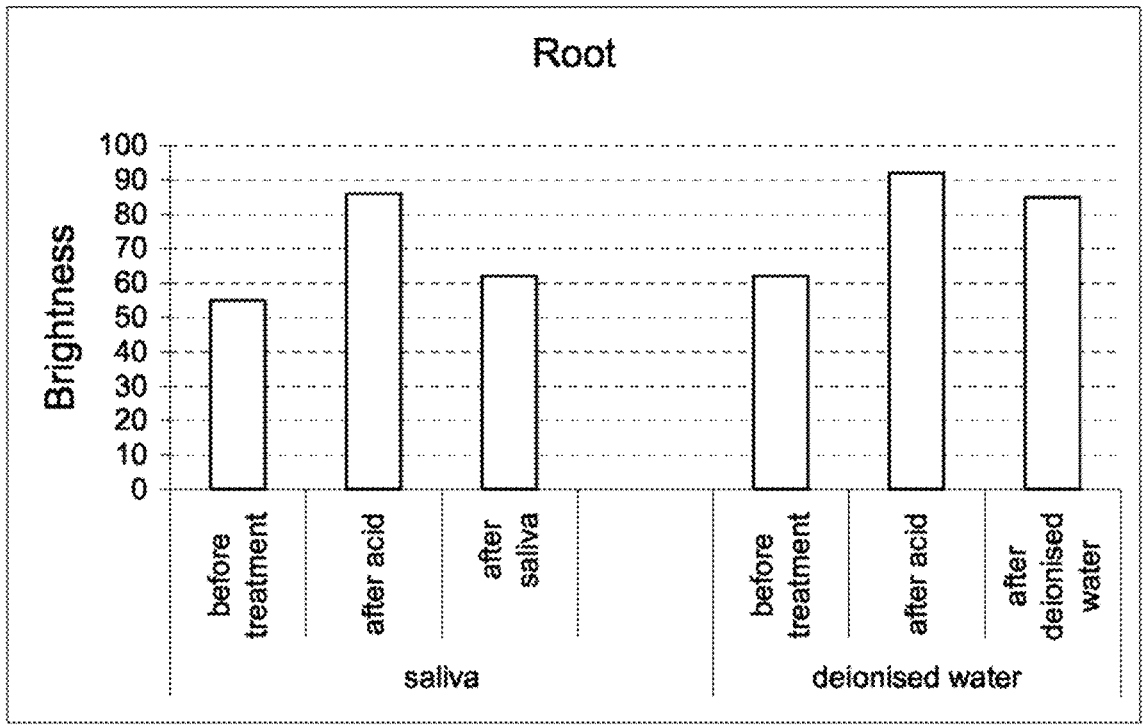

FIGS. 27A and 27B shows how the saliva has a greater protective effect on the acid-treated enamel than deionised water, resulting in a greater reduction in light output. Less difference was observed on the root surface. Together with Experiment L, which provides evidence for the quantitative nature of the assay this suggests that a similar assay whereby a patient's teeth are rinsed with acid solution, light output assessed with a demineralization disclosing solution and the protective affect of saliva determined by reassessing after contact with saliva will provide a method to determine a patient's susceptibility to erosion. This will help in clinical diagnosis, deciding on appropriate treatment and providing evidence for how lifestyle affects a patient's teeth.

Experiment L: Assessment of the Erosivity of Foodstuffs

Different foodstuffs are known to cause different levels of erosion (e.g. Hemingway et al., *British Dental Journal* (2006); 201, 439). This is partly due to the pH of the foodstuff, and partly due to calcium concentration. For example, carbonated soft drinks contain high levels of acid and are known to be a cause of tooth erosion and can exacerbate dentine hypersensitivity.

The disclosing solution and assay method may be used to develop an assay for dental erosion (and indirectly, hypersensitivity). This may be used to identify the extent of demineralisation caused by foodstuffs, so proving a risk factor of foods. It may be used to determine the effectiveness of consumer and clinical products such as toothpastes, mouthwashes, sealants, bleaching agents. It may also be used in the development and identification of foodstuffs that cause less demineralisation and are therefore kinder to teeth.

In hypersensitive teeth, the dentine has more tubules open at the dentine surface (up to 8 times) and the tubule diameter is wider. This provides a greater available surface area for demineralisation, for example by acidic drinks, and will also lead to the release of more calcium following application of such products. This will be observed as a brighter region.

Lines were drawn across extracted deciduous teeth with nail varnish to delimit crown and root surfaces. Extracted teeth were incubated in solutions of various pH. These were either various dilutions of citric acid, sodium bicarbonate, phosphate buffered saline or deionised water. The pH of the solutions was also assessed (with a Hydras 300 pH meter®). Incubations were for 2 minute, after incubation the teeth were removed rinsed in deionised water then assayed. The tooth was imaged with a Sony HX9 camera using 2×2 binning and image capture time of 10 ms in the light. 0.2 $cm^3$ of 1 $mg/cm^3$ aequorin in 1% Akucell 3625 gel (disclosing gel) was prepared with 1 mM EDTA and transferred to tooth with automatic pipettor. A 1 min image with 2×2 binning was taken immediately in the dark. ImageJ was used to determine the brightness of the crown and root areas. Glowell™ (blue G2, 96 well format) were included to ensure the uniformity of the light measuring equipment. Experiments were performed in triplicate; averages are shown.

Figure 28:
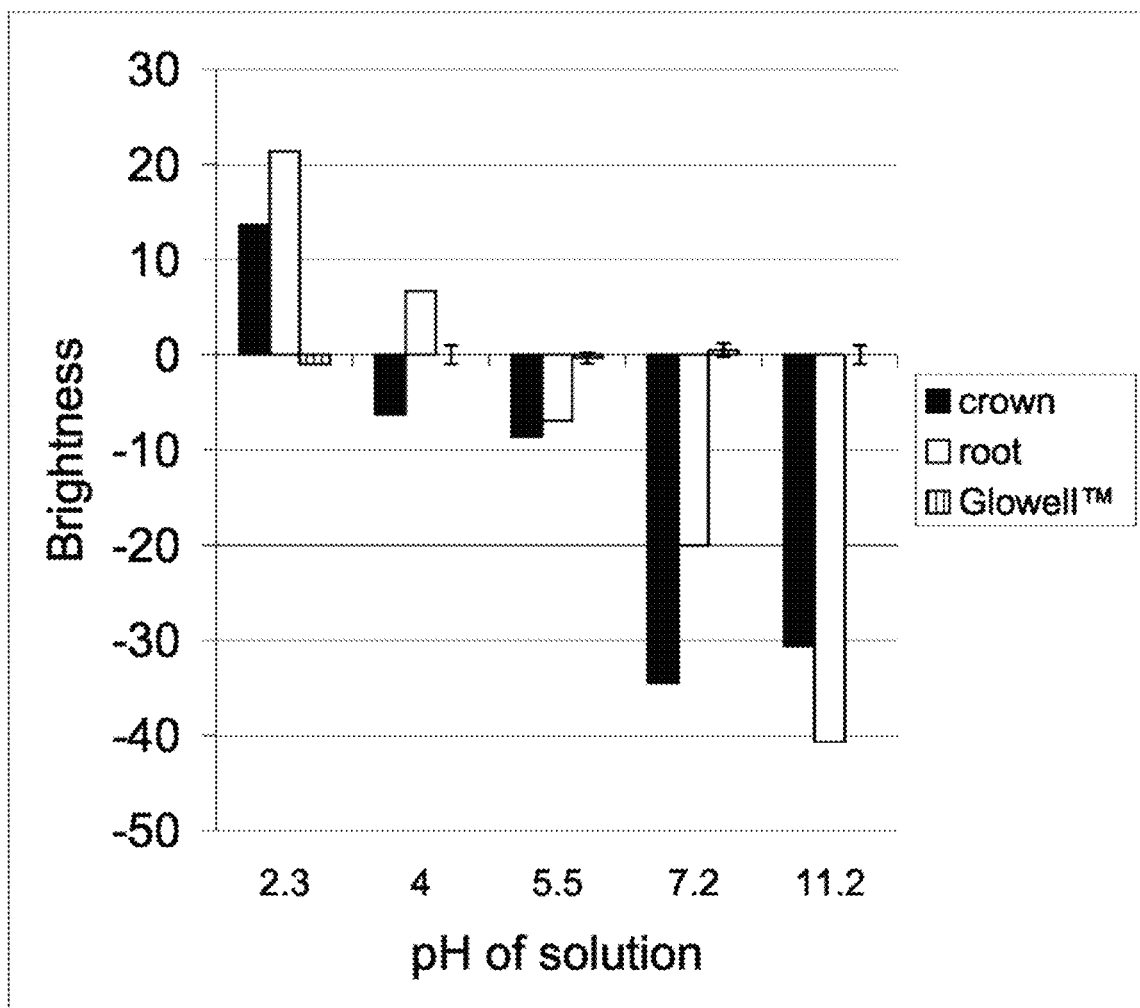
FIG. 28 is a graph showing the effects of solutions of differing pH on different levels of demineralization, as measured by a change in brightness, with solutions of lower pH generating more demineralization (more brightness)

FIG. 28 illustrates how solutions of differing pH lead to different levels of demineralisation, as measured by brightness, with solutions of lower pH generating more demineralisation (more brightness). As shown, the root was more susceptible than crown, with more demineralisation at pH 4, which matches well with the available literature, which indicates that enamel demineralises at a critical pH of 5.5, whereas the root tissue, which is not protected by enamel demineralises at a critical pH of 6.2. This experiment indicates that the assay is quantitative and can be used to assess demineralisation resulting from erosion. Disclosing gels or solutions, which identify demineralisation due to ion release, can be used to indicate tooth damage such as erosion or increased likelihood of hypersensitivity.

Figure 29:
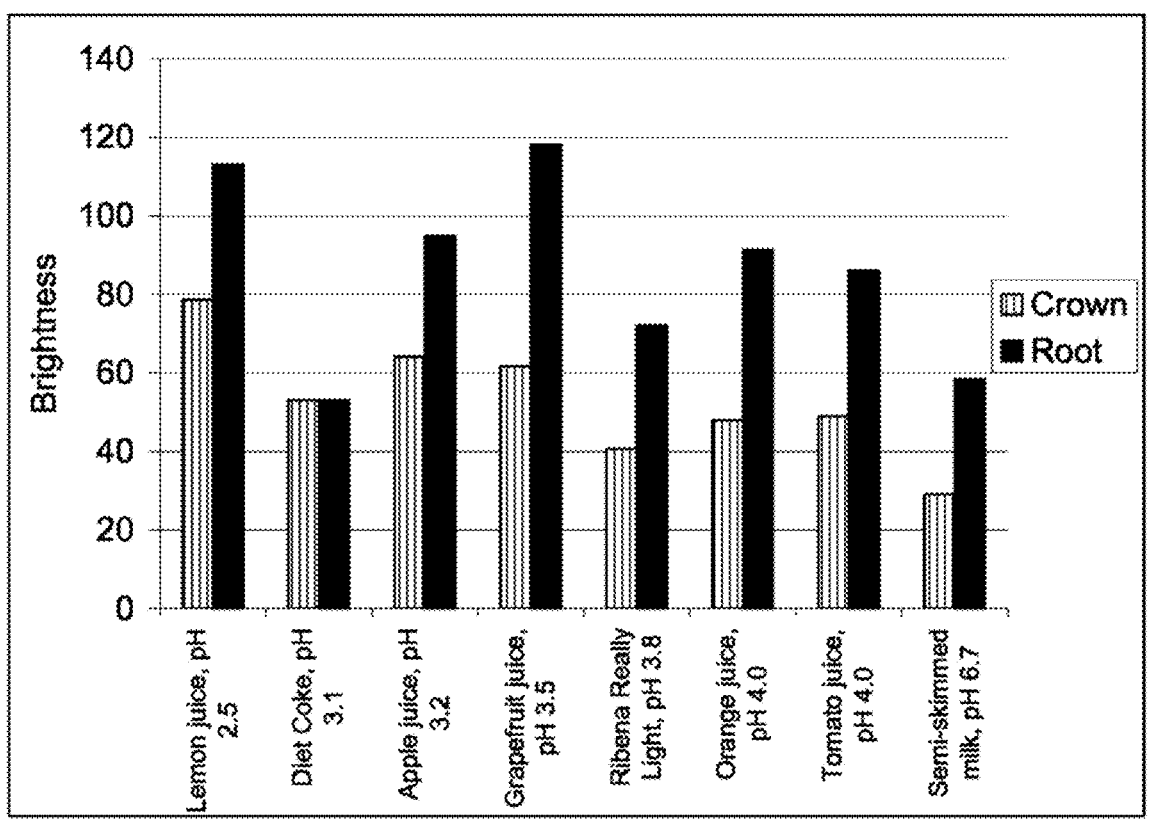
FIG. 29 is a graph indicating that the effect of foodstuffs on demineralization of teeth can be determined using the disclosing composition and assay method of the invention.

FIG. 29 illustrates how the effect of foodstuffs on demineralization of teeth can be determined using this disclosing composition and assay method. Assay method was as described. Results indicate that the pH of the foodstuff has a large affect on the teeth. Again the root surface appears more susceptible to pH. The results were not only dependent on the pH of the foods and other factors appear to be involved. So, the diet drinks coca cola® and ribena really light® produced less light than may be expected from their pH.

Disclosing gels or solutions, which identify demineralization due to ion release when used in an assay such as this, can be used to determine the risk factors of different food stuffs on teeth or as a tool in the development of new food stuffs and consumer and clinical products such as toothpastes, mouthwashes, sealants, bleaching agents. Addition of other steps, such as incorporation of a saliva wash as shown in Experiment G may also be useful to mimic in mouth conditions.

The invention claimed is:

1. A method for the intra-oral detection of active dental caries and/or active tooth demineralisation due to erosion, comprising the steps of:
    exposing a tooth to a pharmaceutical composition comprising proteins or protein complexes which produce a bioluminescent optical signal in the presence of free ions, wherein the protein or protein complex comprises aequorin, obelin, clytin, mitrocomin, halistaurin, phialidin, mnemiopsin, symplectin, gr-bolinopsin, casein, calsequestrin, calexcitin, calcium binding cysteine protease, berovin, or mixtures thereof at a concentration that gives a detectably high signal to noise ratio, and
    detecting the resulting bioluminescent optical signal intra-orally.

2. A method according to claim 1 further comprising the step of determining the location of tooth demineralisation based on the bioluminescent optical signal detected.

3. A method according to claim 1, wherein an image of the tooth is taken using a light source prior to exposing the tooth to the composition.

4. A method according to claim 3, wherein a further image is generated from detection of the bioluminescent optical signal after exposing the tooth to the composition and the further image is superimposed on the image of the tooth taken using a light source prior to exposing the tooth to the composition.

5. A method according to claim 1, wherein an image is generated from detection of the bioluminescent optical signal after exposing the tooth to the composition.

6. A method according to claim 1, further comprising the steps of marking regions of the tooth in order to allow identification of particular regions.

7. A method according to claim 1, further comprising the step of exposing the tooth to a sensitising solution prior to exposure with the composition.

8. A method according to claim 1, wherein the sensitising solution comprises an acidic solution.

9. A method according to claim 7, wherein the sensitising solution comprises a sugar containing solution.

10. A method according to claim 7, wherein a period of time is allowed to lapse in between applying the sensitising solution and applying the pharmaceutical composition.

11. A method according to claim 1, wherein detection is carried out by means of a spectrophotometer, charge coupled device (CCD), complementary metal-oxide semiconductor CMOS, digital camera, intensified camera, intraoral camera, videoscope, photographic film, fibre-optic device, photometric detector, photomultiplier, avalanche photodiode, light sensitive array, micro-electro-mechanical system (MEMS) or a human observer.

12. A method according to claim 1, further comprising differentiating between active and inactive dental caries.

13. A method for the intra-oral detection of active dental caries and/or active tooth demineralisation due to erosion, comprising the steps of:
    exposing a tooth to a pharmaceutical composition comprising proteins or protein complexes which produce a bioluminescent optical signal in the presence of free ions, wherein the protein or protein complex comprises aequorin, obelin, clytin, mitrocomin, halistaurin, phialidin, mnemiopsin, symplectin, gr-bolinopsin, casein, calsequestrin, calexcitin, calcium binding cysteine protease, berovin, or mixtures thereof at a concentration from 1 ng/ml to 10 ng/ml complex, and
    detecting the resulting bioluminescent optical signal.

14. A method according to claim 13 further comprising the step of determining the location of tooth demineralisation based on the bioluminescent optical signal detected.

15. A method according to claim 13, further comprising the steps of marking regions of the tooth or tooth model in order to allow identification of particular regions.

16. A method according to claim 13, further comprising the step of exposing the tooth to a sensitising solution prior to exposure with the composition.

17. A method according to claim 13, wherein the sensitising solution comprises an acidic solution.

18. A method according to claim 16, wherein the sensitising solution comprises a sugar containing solution.

19. A method according to claim 16, wherein a period of time is allowed to lapse in between applying the sensitising solution and applying the pharmaceutical composition.

20. A method according to claim 13, further comprising differentiating between active and inactive dental caries.

21. The method according to claim 1, wherein exposing a tooth to a pharmaceutical composition further comprises applying the pharmaceutical composition intra-orally.

22. The method according to claim 13, wherein exposing a tooth to a pharmaceutical composition further comprises applying the pharmaceutical composition intra-orally.

* * * * *